US010378014B2

(12) United States Patent
Dale et al.

(10) Patent No.: US 10,378,014 B2
(45) **Date of Patent: *Aug. 13, 2019**

(54) COMPOSITIONS AND METHODS FOR THE TREATMENT OF INFLUENZA INFECTION

(71) Applicant: Lakewood Amedex, Inc., Sarasota, FL (US)

(72) Inventors: Roderic M.K. Dale, Wilsonville, OR (US); Lun-Quan Sun, Sydney (AU)

(73) Assignee: Lakewood Amedex, Inc., Sarasota, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/400,797

(22) Filed: Jan. 6, 2017

(65) Prior Publication Data

US 2017/0191062 A1 Jul. 6, 2017

Related U.S. Application Data

(63) Continuation of application No. 11/458,378, filed on Jul. 18, 2006, now Pat. No. 9,574,243.

(30) Foreign Application Priority Data

Jan. 17, 2006 (CN) .......................... 2006 1 0000900

(51) Int. Cl.

*C07K 14/005* (2006.01)
*A61K 38/00* (2006.01)
*A61K 39/145* (2006.01)
*C12N 15/113* (2010.01)
*C12Q 1/70* (2006.01)

(52) U.S. Cl.

CPC .......... *C12N 15/1131* (2013.01); *A61K 38/00* (2013.01); *C07K 14/005* (2013.01); *C12Q 1/701* (2013.01); *A61K 39/145* (2013.01); *C12N 2310/11* (2013.01); *C12N 2310/321* (2013.01); *C12N 2320/32* (2013.01)

(58) Field of Classification Search

None

See application file for complete search history.

(56) References Cited

U.S. PATENT DOCUMENTS

| | | | | | |
|---|---|---|---|---|---|
| 6,117,992 | A * | 9/2000 | Iyer | C07H 21/00 536/25.3 |
| 7,037,707 | B2 * | 5/2006 | Webster | C07H 21/04 424/206.1 |
| 9,574,243 | B2 * | 2/2017 | Dale | C12Q 1/701 |
| 2003/0207834 | A1 * | 11/2003 | Dale | C12N 15/113 514/44 R |
| 2004/0242518 | A1 * | 12/2004 | Chen | C12N 15/1131 514/44 A |
| 2007/0197460 | A1 * | 8/2007 | Fougerolles | C12N 15/1131 514/44 A |

FOREIGN PATENT DOCUMENTS

WO WO/05/014812 * 2/2005

* cited by examiner

*Primary Examiner* — Benjamin P Blumel

(74) *Attorney, Agent, or Firm* — Taft Stettinius & Hollister LLP

(57) ABSTRACT

The invention provides compositions of oligonucleotides targeted at influenza genes and at host animal genes involved in response to influenza infection. In some embodiments, the oligonucleotides are modified. In some embodiments, the compositions contain one, or more than one, oligonucleotide. The invention also provides methods and kits using the compositions of the invention for the treatment and prevention of influenza.

21 Claims, 4 Drawing Sheets

Specification includes a Sequence Listing.

COMPOSITIONS AND METHODS FOR THE TREATMENT OF INFLUENZA INFECTION

CROSS-REFERENCE

The present application is a continuation of U.S. patent application Ser. No. 11/458,378, filed Jul. 18, 2006, and also claims the priority benefit of Chinese Patent Application Serial No. CN200610000900.1, filed on Jan. 17, 2006, the text and drawings of which are hereby incorporated by reference in their entireties.

BACKGROUND OF THE INVENTION

Influenza virus infection is a major public health problem, causing millions of cases of severe illness and as many as 500,000 deaths each year worldwide (WHO report, 2004, A56/23). Influenza virus has A, B and C types, among which the type A can be further classified into many sub-types according to the variations in NA and HA genes. Thus far, there have been 15 HA subtypes and 9 NA subtypes and the different combinations between HA and NA subtypes can form many types of influenza A virus subtypes.

Although inactivated vaccines are 60-80% effective against the matched influenza strains, vaccination coverage is a problem worldwide. Moreover, this strategy provides no protection against unexpected strains, outbreaks such as the H5 and H7 avian influenza outbreaks in Hong Kong in 1997 and the Netherlands and Southeast Asia in 2003-2004, or pandemics. Currently, antiviral drugs are the best defense against these outbreaks, but they provide only partial protection (Nicholson, etc., Lancet, 355:1845-1850, 2000), usually companied with some side effects, especially to the central nervous system (Wenzel, JAMA, 283:1057-1059, 2000).

SUMMARY OF THE INVENTION

The present invention relates to treatment of influenza infection using oligonucleotide compositions. Said oligonucleotide compositions comprise modified oligonucleotides containing 7 to 75 contiguous ribose groups linked by achiral 5' to 3' internucleoside phosphate linkages, wherein the modified oligonucleotide is complementary to a region of influenza virus genes and/or the host genes involved in response to influenza infection. The present invention thus relates to one or more polynucleotides each of which is designed to hybridize to one of the gene sequences selected from the group consisting of influenza viral genes and animal host genes involved in response to influenza infection, preferably the group consisting of the genes listed in Table 1. The modified oligonucleotide hybridizes to one of said gene sequences under stringent conditions, thereby suppressing expression of the corresponding gene product(s). In other embodiments, the composition contains two, three, four, five, or more than five different modified oligonucleotides. In still other embodiments, the modified oligonucleotide is complementary to a region of the influenza viral genes and the host genes consisting of the 5' UTR region, translational start site, the 3' UTR, and translational termination site. In some embodiments, the modified oligonucleotide has a $T_m$ of about 75-115° C. at a concentration of 1 mM and a length of 10 to 26 bases, or a $T_m$ of about 40° C. to 85° C. at a concentration of 1 pM and a length of 10 to 26 bases. Preferred compositions include antisense oligonucleotides. Some preferred compositions contain microRNA.

The present invention provides compositions and methods for the suppression of expression of influenza genes and the animal host genes that code for gene products that are involved in the interactions between the virus and host. In some embodiments the interactions between the virus and the animal host are virally-induced inflammation and apoptosis.

One aspect of the invention provides compositions and methods for treating influenza infection. These compositions are suitable for administration to an animal, which in some preferred embodiments, the animal is a mammal. In some preferred embodiments the animal is a human, and in other preferred embodiments the animal comprises avian species.

In some embodiments, the invention provides a composition suitable for administration to an animal comprising a modified oligonucleotide containing 7 to 75 contiguous ribose groups linked by achiral 5' to 3' internucleoside phosphate linkages, wherein the modified oligonucleotide is complementary to a region of a gene coding for an influenza virus or a host gene involved in inflammatory or apoptotic response to influenza infection. In some embodiments, the composition contains two, three, four, five, or more than five different modified oligonucleotides. In other embodiments, the oligonucleotide comprises about seven to seventy-five nucleotides containing seven or more contiguous ribose groups linked by achiral 5' to 3' internucleoside phosphate linkages. In still other embodiments, the modified oligonucleotide is complementary to a region of the influenza genes and/or the animal host genes consisting of the 5' UTR region, translational start site, the 3' UTR, translational termination site and transcription site. In one of the preferred embodiments, the modified oligonucleotide has a $T_m$ of about 75-115° C. at a concentration of 1 mM and a length of 10 to 26 bases, or a $T_m$ of about 40° C. to 85° C. at a concentration of 1 pM and a length of 10 to 26 bases. The modified oligonucleotides comprise ribonucleotides and deoxyribonucleotides. In instances, the ribose group of the oligonucleotide has a modified 2' substituent; in some embodiments the modified substituent is selected from the group consisting of hydrogen, methoxy, propoxy, methoxyethoxy, fluorine, chlorine, bromine and iodine. In other instances, the modified oligonucleotide is 3' end-blocked. In some embodiments, the modified oligonucleotide is 5' end-blocked. In other embodiments, the modified oligonucleotide is 3' end-modified. In still other embodiments, the modified oligonucleotide is 5' end-modified. In some embodiments, the invention provides an antisense oligonucleotide, e.g. an antisense oligonucleotide that is complementary to an influenza gene and/or a host gene involved in response to influenza infection. A preferred embodiment of the invention provides an oligonucleotide that is microRNA. In particularly preferred embodiments of the invention, at least one oligonucleotide is provided that inhibits the expression of the influenza genes and host genes involved in response to infection by influenza, wherein the oligonucleotide is selected from the group consisting of SEQ ID NOS: 1-110.

In still other embodiments, the invention provides a composition for the suppression of expression of the influenza genes and animal host genes involved in response to influenza infection comprising two or more gene-modulating oligonucleotides, wherein at least one oligonucleotide is targeted to influenza viral genes, and at least one oligonucleotide is targeted to an animal host gene. In some embodiments the animal host gene is a gene coding for a protein selected from the group consisting of Fas, Fas-L, TACE, TNF-R1, TNT-α, Caspase-3, Rantes, IL-1b, IL-18, P38

MAPK, CXCL-1, IP-10. (Table 1). In some embodiments the composition contains one or more antisense oligonucleotides, targeted to influenza viral genes and host genes, selected from the oligonucleotides shown in Tables 2, 3 and 4. In some embodiments, the compositions contain at least one antisense oligonucleotide targeted to more than one region of a single influenza viral gene, and at least one antisense oligonucleotide targeted to an animal host gene that is involved in response to influenza infection. In some embodiments the animal host gene involved in response to influenza infection regulates inflammation or apoptosis. In some embodiments, the compositions contain more than one oligonucleotide targeted to multiple influenza genes. In some embodiments, said more than one oligonucleotide is chosen from SEQ ID NOS: 1-37. In some embodiments the composition contains more than one oligonucleotide targeted to influenza genes and also contains at least one oligonucleotide targeted to animal host genes that are involved in response to influenza infection. In some embodiments the composition contains more than one oligonucleotide targeted to influenza genes and also contains more than one oligonucleotide targeted to animal host genes that are involved in response to influenza infection. In some embodiments, said more than one oligonucleotide targeted to influenza genes target genes shown in Table 1. In some embodiments, said more than one oligonucleotide targeted to animal host genes involved in response to influenza infection target genes shown in Table 1. In some embodiments, said more than one oligonucleotide targeted to influenza genes is an oligonucleotide wherein the sequence is chosen from SEQ ID NOS: 1-37. In some embodiments, said more than one oligonucleotide targeted to animal host genes involved in response to influenza infection is an oligonucleotide wherein the sequence is chosen from SEQ ID NOS: 38-110.

In some embodiments, the invention provides a method of treating influenza infection comprising administering to an animal suffering from influenza an effective amount of a composition of the invention. In another embodiment, the invention provides a method of suppressing expression of the influenza viral genes and the host genes in an animal comprising administering to the animal an oligonucleotide wherein the oligonucleotide is administered at a dose of 0.01;
0.02; 0.03; 0.04; 0.05; 0.06; 0.07; 0.08; 0.09; 0.1; 0.5; 1.0; 1.5; 2.0; 3.0; 4.0; 5.0; 7.5; 10.0; 12.5; 15.0; 17.5; 20.0; 22.5; 25.0; 27.5; 30.0; 32.5; 35.0; 37.5; 40.0; 42.5; 45.0; 47.5; 50.0; 52.5; 55.0; 57.5; 60.0; 62.5; 65.0; 67.5; 70.0; 72.5; 75.0; 77.5; 80.0; 82.5; 85.0; 87.5; 90.0; 92.5; 95.0; 97.5 to 100 mg/kg. In some of these embodiments, the animal is an avian species. In some of these embodiments, the animal is a human.

In still yet another embodiment, the invention provides a method of suppressing expression of influenza viral genes in an animal comprising administering a first gene-modulating oligonucleotide and a second gene-modulating oligonucleotide, wherein the first oligonucleotide suppresses the expression of an influenza viral gene transcript and the second oligonucleotide modulates the expression of a host gene selected from the group consisting of an influenza gene and a non-influenza gene. In some of these embodiments, the animal is an avian species. In some of these embodiments, the animal is a human.

In some embodiments of the invention, antisense oligonucleotides of the present invention display greater than or equal to 60, 70, 80, 90, 95, or 99 percent sequence identity to a nucleotide sequence selected from the group of SEQ ID NOS: 1-110. In some embodiments, the oligonucleotide exhibits a sequence difference of one, two, or more nucleotide units from that of the sequence selected from SEQ ID NOS: 1-110 and provides base pairing to effectively suppress expression of the targeted gene. In other embodiments, the oligonucleotide exhibits up to 30% mismatches from the nucleotide sequence selected from the group of SEQ ID NOS: 1-110, and provides effective suppression of the targeted gene.

In some embodiments, compositions of the invention provide for a mixture of oligonucleotides that target strain variants of a particular region of an influenza viral gene. These variants differ by one, two, or more nucleotides from the sequence of the predominate strain. In some embodiments, these variants differ by one, two, or more nucleotides from the sequences of SEQ ID NOS: 1-37. In some embodiments, compositions of the invention provide at least one additional oligonucleotide which is targeted to a second viral gene or to an animal host gene that is involved in response to influenza infection. In some embodiments, compositions of the invention provide more than one additional oligonucleotide which is targeted to a second viral gene or to an animal host gene that is involved in response to influenza infection.

In another embodiment, the invention provides a method of treating an animal or human suffering from influenza infection comprising administering to human and the animal an oligonucleotide that modulates the expression of an influenza gene, wherein the oligonucleotide is administered at a dose of 0.001; 0.02; 0.03; 0.04; 0.05; 0.06; 0.07; 0.08; 0.09; 0.1; 0.5; 1.0; 1.5; 2.0; 3.0; 4.0; 5.0; 7.5; 10.0; 12.5; 15.0; 17.5; 20.0; 22.5; 25.0; 27.5; 30.0; 32.5; 35.0; 37.5; 40.0; 42.5; 45.0; 47.5; 50.0; 52.5; 55.0; 57.5; 60.0; 62.5; 65.0; 67.5; 70.0; 72.5; 75.0; 77.5; 80.0; 82.5; 85.0; 87.5; 90.0; 92.5; 95.0; 97.5 to 100 mg/kg. In some preferred embodiments, the animal is a human. In some preferred embodiments, the animal comprises an avian species.

The invention also provides a method of treating an animal or human suffering from influenza infection comprising administering to the animal or human a first gene-modulating oligonucleotide and a second gene-modulating oligonucleotide, wherein the first oligonucleotide suppresses the expression of an influenza gene and the second oligonucleotide modulates the expression of a gene from the group consisting of an influenza gene and an animal host gene that is involved in response to influenza infection.

In some embodiments, a composition suitable for administration to an animal is disclosed, comprising: at least one modified antisense oligonucleotide containing about 12 to about 26 contiguous ribose groups linked by achiral 5' to 3' internucleoside phosphodiester linkages, wherein at least one ribose group of said at least one modified antisense oligonucleotide has a modified 2' substituent; one or both of the 5' and 3' ends of said at least one modified antisense oligonucleotide are end-blocked; said at least one modified antisense oligonucleotide is complementary to a region of an influenza viral gene; and an excipient. In some embodiments, said one or both of the 5' and 3' ends of said at least one modified antisense oligonucleotide are end-blocked with an alkyl or an alcohol group.

In some embodiments, said composition comprises a plurality of modified oligonucleotides. In some embodiments, said plurality of oligonucleotides comprise: more than one oligonucleotide targeted to a first influenza viral gene, wherein each of said more than one oligonucleotide targeted to a first influenza viral gene is independently complementary to the 5' UTR region, translational start site, the 3' UTR, or translational termination site of said first influenza viral gene; and at least one oligonucleotide targeted to a second influenza viral gene, wherein each of said at least one oligonucleotide targeted to a second influenza viral gene is independently complementary to the 5' UTR region, translational start site, the 3' UTR, translational termination site or transcription start site of said second influenza viral gene. In some embodiments, each of said plurality of oligonucleotides is an antisense oligonucleotide.

In some embodiments, each of said more than one oligonucleotides targeted to said first influenza viral gene is an antisense oligonucleotide. In some embodiments, each of said at least one oligonucleotides targeted to said second influenza viral gene is an antisense oligonucleotide. In some embodiments, said more than one oligonucleotide targeted to said first influenza viral gene comprises a combination of oligonucleotides complementary to the 5' UTR region, translational start site, the 3' UTR, and translational termination site of said first influenza viral gene. In some embodiments, said at least one oligonucleotide targeted to said second influenza viral gene comprises a combination of oligonucleotides complementary to the 5' UTR region, translational start site, the 3' UTR, translational termination site and transcription start site of said second influenza viral gene.

In some embodiments, said influenza viral gene is NS1. In some embodiments, at least one modified oligonucleotide comprises SEQ ID NO: 21. In some embodiments, said composition is suitable for oral administration. In some embodiments, said 2' substituent is selected from the group consisting of methoxy, propoxy, and methoxy-ethoxy. In some embodiments, one or both of said 3' and said 5' ends comprise a butanol. In some embodiments, said animal is human. In some embodiments, each ribose group of said at least one modified antisense oligonucleotide comprises a modified 2' substituent. In some embodiments, said 2' substituent of each said ribose group is methoxy, propoxy, or methoxy-ethoxy.

In some embodiments, said 2' substituent of each said ribose group is methoxy, propoxy, methoxy-ethoxy, fluorine, chlorine, bromine, or iodine. In some embodiments, said composition is suitable for nasal administration. In some embodiments, said composition is suitable for parenteral administration.

In some embodiments, said at least one modified antisense oligonucleotide is a single modified antisense oligonucleotide, such that said composition comprises one modified antisense oligonucleotide. In some embodiments, said single modified antisense oligonucleotide contains about 12 to about 26 contiguous ribose groups linked by achiral 5' to 3' internucleoside phosphodiester linkages, and wherein each ribose group of said single modified antisense oligonucleotide comprises a 2'-O-methyl substitution; the 3' end of said single modified antisense oligonucleotide comprises a butanol end-blocking group; and said single modified antisense oligonucleotide is complementary to a region of a H5N1 influenza virus gene that encodes a NS1 protein. In some embodiments, said single modified antisense oligonucleotide comprises nucleotides having the sequence of SEQ ID NO. 4, 5, 6, 7, 14, 20, 21, 111, 112, 113, or 114. In some embodiments, said single modified antisense oligonucleotide comprises nucleotides having the sequence of SEQ ID NO. 15, 16, 17, 18, 19, or 21.

In some embodiments, a method of treating an animal suffering from an influenza infection is disclosed, comprising administering to said animal a composition comprising: at least one modified antisense oligonucleotide containing about 12 to about 26 contiguous ribose groups linked by achiral 5' to 3' internucleoside phosphodiester linkages, wherein at least one ribose group of said at least one modified antisense oligonucleotide has a modified 2' substituent; one or both of the 5' and 3' ends of said at least one modified antisense oligonucleotide are end-blocked; said at least one modified antisense oligonucleotide is complementary to a region of an influenza viral gene; and an excipient. In some embodiments, said one or both of the 5' and 3' ends of said at least one modified antisense oligonucleotide are end-blocked with an alkyl or an alcohol group. In some embodiments, said 2' substituent of each said ribose group is methoxy, propoxy, methoxy-ethoxy, fluorine, chlorine, bromine, or iodine.

In some embodiments, said composition comprises a plurality of modified oligonucleotides. In some embodiments, said plurality of oligonucleotides comprises: more than one oligonucleotide targeted to a first influenza viral gene, wherein each of said more than one oligonucleotide targeted to a first influenza viral gene is independently complementary to the 5' UTR region, translational start site, the 3' UTR, or translational termination site of said first influenza viral gene; and at least one oligonucleotide targeted to a second influenza viral gene, wherein each of said at least one oligonucleotide targeted to a second influenza viral gene is independently complementary to the 5' UTR region, translational start site, the 3' UTR, translational termination site or transcription start site of said second influenza viral gene.

In some embodiments, said influenza viral gene is NS1. In some embodiments, at least one modified oligonucleotide comprises SEQ ID NO: 21. In some embodiments, said composition is administered orally. In some embodiments, said 2' substituent is selected from the group consisting of methoxy, propoxy, and methoxy-ethoxy. In some embodiments, one or both of said 3' and said 5' ends comprise a butanol. In some embodiments, said animal is human. In some embodiments, each ribose group of said at least one modified oligonucleotide comprises a modified 2' substituent. In some embodiments, said 2' substituent of each said ribose group is methoxy, propoxy, methoxy-ethoxy, fluorine, chlorine, bromine, or iodine. In some embodiments, said composition is administered nasally. In some embodiments, said administration is parenteral.

In some embodiments, each of said plurality of oligonucleotides is an antisense oligonucleotide. In some embodiments, each of said more than one oligonucleotides targeted to said first influenza viral gene is an antisense oligonucleotide. In some embodiments, each of said at least one oligonucleotides targeted to said second influenza viral gene is an antisense oligonucleotide. In some embodiments, said more than one oligonucleotide targeted to said first influenza viral gene comprises a combination of oligonucleotides complementary to the 5' UTR region, translational start site, the 3' UTR, and translational termination site of said first influenza viral gene. In some embodiments, said at least one oligonucleotide targeted to said second influenza viral gene comprises a combination of oligonucleotides complementary to the 5' UTR region, translational start site, the 3' UTR, translational termination site and transcription start site of said second influenza viral gene.

In some embodiments, said at least one modified antisense oligonucleotide is a single modified antisense oligonucleotide, such that said composition comprises one modified antisense oligonucleotide. In some embodiments, said single modified antisense oligonucleotide contains about 12 to about 26 contiguous ribose groups linked by achiral 5' to 3' internucleoside phosphodiester linkages, and wherein each ribose group of said single modified antisense oligonucleotide comprises a 2'-O-methyl substitution; the 3' end of said single modified antisense oligonucleotide comprises a butanol end-blocking group; and said single modified antisense oligonucleotide is complementary to a region of a H5N1 influenza virus gene that encodes a NS1 protein. In some embodiments, said single modified antisense oligonucleotide comprises nucleotides having the sequence of SEQ ID NO. 4, 5, 6, 7, 14, 20, 21, 111, 112, 113, or 114. In some embodiments, said single modified antisense oligonucleotide comprises nucleotides having the sequence of SEQ ID NO. 15, 16, 17, 18, 19, or 21.

INCORPORATION BY REFERENCE

All publications and patent applications mentioned in this specification are herein incorporated by reference to the same extent as if each individual publication or patent application was specifically and individually indicated to be incorporated by reference

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
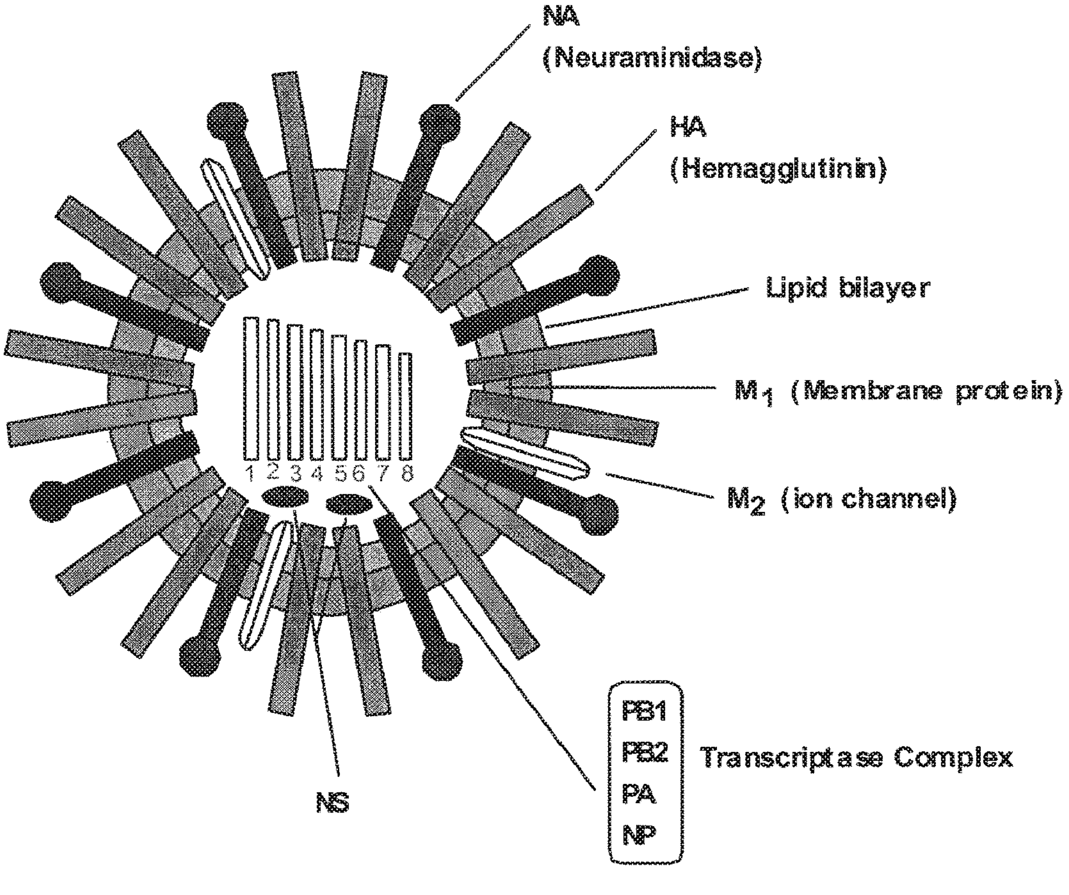
FIG. 1 is a schematic representation of a virus illustrating the location of genes targeted by the compositions of the invention.

The present invention provides compositions and methods for the suppression and modulation of expression of genes that code for influenza viral gene products and animal host gene products that are involved in influenza infection and host response. Accordingly, the invention provides compositions and methods for using the compositions, for suppression of influenza infection and treatment of influenza infection symptoms. The invention also provides compositions and methods of using the compositions prophylactically for preventing influenza infection and associated symptoms.

Generally, the compositions and methods of the invention utilize oligonucleotides that modulate gene expression, also referred to herein as "gene modulators" and "gene-modulating oligonucleotides." Exemplary gene modulators of the invention include antisense oligonucleotides, interfering RNA (RNAi), micro RNA (miRNA), ribozymes, and DNAzymes. In some embodiments, the invention provides a single gene modulator targeted at a single gene involved in influenza infection, e.g., NS1. In other embodiments, the invention provides combinations of gene modulators. These combinations include: combinations of different types of gene modulators, combinations of gene modulators targeted to different parts of the same gene, and combinations of gene modulators targeted to different genes, as well as combinations of any of the aforementioned combinations.

The invention further provides modified oligonucleotides for use in any of the above compositions. In some preferred embodiments, oligonucleotides used in the invention can be, e.g., end-blocked, protonated, exhibit substantial acid resistance, substantial nuclease resistance, and/or contain achiral internucleoside phosphate linkages and modified ribose or deoxyribose substituents.

The invention further provides methods using the compositions of the invention. Methods include methods of treating animals (e.g., humans and members of avian species) by suppressing gene expression in cells by contacting cells with compositions of the invention. Methods also include methods of treatment of symptoms using the gene modulating compositions of the invention. Symptoms for treatment include all influenza infection associated conditions. In addition, the invention provides methods of preventing influenza infection in animals.

In addition, the invention provides kits that provide compositions of the invention, optionally including instructions for use of the compositions in methods of the invention.

The gene modulators of the invention include antisense oligonucleotides. Compositions of the invention contain one or more gene modulators that is/are targeted to one or more areas of one or more genes. A composition containing a nucleic acid "modulates" or is "capable of modulating" or is a "modulator" of gene expression if the nucleic acid modulates gene expression directly or if the nucleic acid encodes a gene product that modulates gene expression. As used herein, the term "modulate" includes inhibition and stimulation, as well as other changes (e.g., production of a modified gene product) in gene expression. The term "inhibition" is intended to include both complete and partial inhibition of expression. In various embodiments, gene expression is inhibited to a level at least about 1% to 99%, or at least 1%, 5, 10%, 20%, 30%, 40%, 50%, 60%, 70%, 80%, 90, 95%, 97%, 98%, or 99% lower than the wild type level of gene expression. In some embodiments, expression is inhibited to a level at least about 1% to 99%, or at least 1%, 5, 10%, 20%, 30%, 40%, 50%, 60%, 70%, 80%, 90, 95%, 97%, 98%, or 99% lower than the wild type level of gene expression.

Genes may be chosen for modulation based on their involvement in one or more pathways related to influenza infection to be treated. In some embodiments, the invention provides compositions that contain a gene modulator targeted to one area of one gene, e.g., NS1. In some embodiments, the invention provides gene modulators that are targeted to more than one area of a single gene, e.g., NS1. In some embodiments, the invention provides gene modulators that are targeted to multiple genes, e.g., NS1 and host gene IP-10 genes, as well as other genes described herein (Table 1). In these embodiments, more than one area of a gene may be targeted.

I. Compositions of the Invention

The compositions of the invention include one or more agents capable of modulating expression of a viral influenza gene or genes associated with influenza infection, and the host genes that are involved in response to influenza infection. Typically, the gene modulators of the invention are inhibitory to gene expression and include, without limitation, antisense oligonucleotides, interfering RNA (RNAi), micro RNA (miRNA), ribozymes, and DNAzymes. Compositions of the invention contain one or more gene modulators that is/are targeted to one or more areas of one or more genes. In some embodiments, the invention provides compositions that contain a gene modulator targeted to one area of one gene, e.g., NSI. In some embodiments, the invention provides gene modulators that are targeted to more than one area of one gene, e.g., NSI. In some embodiments, the invention provides gene modulators that are targeted to multiple genes, e.g., NSI, PA, and/or PB1. In these embodiments, more than one area of a gene may be targeted.

In preferred embodiments, the invention provides compositions that contain combinations of gene modulators for viral genes and gene modulators for host genes which are responsible for response to infection by influenza virus. These combinations include: combinations of different types of gene modulators, combinations of gene modulators targeted to different parts of the same gene, and combinations of gene modulators targeted to different genes, as well as combinations of any of the aforementioned combinations.

The invention further provides modified oligonucleotides for use in any of the above combinations. In embodiments, oligonucleotides used in the invention can be, e.g., end-blocked, protonated, exhibit substantial acid resistance, substantial nuclease resistance, and/or contain achiral internucleoside phosphate linkages and modified ribose or deoxyribose substituents.

The compositions and methods of the invention may be applied to any gene for which it is desired to alter expression in order to provide a therapeutic effect treating influenza infection, or to prevent influenza infection in an animal. In general, the major targets are genes involved in viral infection and replication, and genes involved in host response to such infection; however, in the majority of cases, several pathways involving multiple genes are affected by, and the invention provides not only compositions and methods targeted to single genes (e.g., NSI) but also compositions and methods targeted to multiple genes, or to multiple areas on a single gene, or both. Compositions and methods are also targeted to multiple genes of both virus and host animals, multiple areas on a single virus gene, multiple areas of genes responsible for host response to viral infection, or both.

A. Expression-Modulating Compositions

Any type of nucleic acid-based therapeutics that modulates expression of a gene may be used in the compositions and methods of the invention. These include antisense oligonucleotides, ribozymes, interfering RNA (RNAi), micro RNA (miRNA), and DNAzymes. Each of these approaches has one central theme in common, that is, the recognition of their target DNA or mRNA sequences via Watson-Crick base-pairing. The present invention thus relates to one or more polynucleotides each of which hybridizes to one of the gene sequences described herein, preferably under stringent conditions. A stringent condition refers to a condition that allows nucleic acid duplexes to be distinguished based on their degree of mismatch, e.g., conditions of temperature and salt concentrations which yield the desired level of discrimination in the hybridization. Such polynucleotides (e.g., antisense, micro RNA (miRNA), and RNAi) can be used to inhibit the expression of influenza infection-associated gene product. Such polynucleotides can also serve as probes and primers for research and diagnostic purposes.

The term “oligonucleotides” as used herein, refers to a molecule comprising nucleotides (i.e., ribonucleotides, deoxyribonucleotides, or both). The term includes monomers and polymers of ribonucleotides and deoxyribonucleotides, or mixtures thereof, with the nucleotides being connected together via, for example 5' to 3' linkages, 5' to 2' linkages, etc. The nucleotides used in the oligonucleotides may be naturally occurring or may be synthetically produced analogues that are capable of forming base-pair relationships with naturally occurring base pairing nucleotides. Examples of non-naturally occurring bases that are capable of forming base-pairing relationships include, but are not limited to, aza and deaza pyrimidine analogues, aza and deaza purine analogues, and other heterocyclic base analogues, wherein one or more of the carbon and nitrogen atoms of the purine and pyrimidine rings have been substituted by heteroatoms, e.g., oxygen, sulfur, selenium, phosphorus, and the like.

1. Antisense Oligonucleotides

Antisense oligonucleotides contain short, chemically synthesized DNA or RNA oligonucleotides with base-pair complementarily against the mRNA target of interest. Without wishing to be limited by theory, it is generally believed that antisense oligonucleotides act to inhibit gene expression by blocking translation of mRNA or by targeting the RNA for degradation by RNase H. Antisense oligonucleotides can block splicing, translation, or nuclear-cytoplasmic transport. The mechanisms of action of antisense oligonucleotides vary depending on the backbone of the oligonucleotide. Antisense oligonucleotides can be complementary to an entire coding region or only to a portion thereof.

An antisense oligonucleotide herein can be, for example, about 5, 10, 15, 20, 25, 30, 35, 40, 45, 50, 60, 70, 80, 90, 100, or more than 100 nucleotides in length. Preferably, the oligonucleotide is about five to about 75 nucleotides in length. The oligonucleotide can also be about eight to about 40, or about 10 to about 30, or about 15 to about 30 sequential nucleotides in length. In one embodiment, the oligonucleotide is about 12 to about 26 nucleotides in length.

Typically, the procedure for designing an antisense oligonucleotide of this invention includes: (i) selecting an oligonucleotide that is adjacent to or overlaps a target region of a gene, (ii) determining the Gibbs Free energy value associated with the oligonucleotide in reference to the target gene, (iii) assessing $T_m$ in reference to the target gene, and (iv) performing a sequence database search to determine whether the oligonucleotide overlaps the 5' UTR, the translational start sequence, the 3' UTR, or the translational termination site of an mRNA of a gene different from the target gene.

Accordingly, in some embodiments, the antisense oligonucleotides of the present invention can be directed to a translational start site, a 5' UTR, a 3' UTR, a termination site or a transcription start site of a target gene. Preferably, the oligonucleotide is adjacent to or overlaps the translational start site of the targeted gene by at least about one base. Still more preferred, the oligonucleotide overlaps the translational start site by at least about two bases. Still more preferred, the oligonucleotide overlaps the translational start site by at least about three bases. Still more preferred, the oligonucleotide overlaps the transcription start site.

It is generally preferable to design an RNA or DNA that has the same or similar base sequence as a portion of the complement of a gene that encodes the 5' end of an RNA. However, a nucleic acid may also have, for example, a same or similar base sequence as other regions of the gene, such as the region encoding a translation start site or the 3' untranslated region. In another example, a nucleic acid may be designed to reflect the region around a splice donor or splice acceptor site, either with or without the intervening intron.

Suitable antisense oligonucleotides for the present invention can be determined by evaluating the Delta G or Gibbs Free energy of oligonucleotide binding to the complementary RNA strand at 37° C. and the $T_m$. The Gibbs Free energy and $T_m$ are measured from the part of the target gene that corresponds to the RNA oligonucleotide that is added. These values can be calculated using, e.g., the program found on ftp://rna.chem.rochester.edu and are described in Matthews et al. (1999) J. Mol. Biol. 288, 911-940 and Matthews et al. (1999) RNA 5, 1458-1469.

Accordingly, some preferred embodiments of the invention provides a composition comprising an oligonucleotide, (i) wherein said oligonucleotide is about 10 to about 30 nucleotides in length, (ii) the Gibbs Free energy of the binding of said oligonucleotide/RNA target duplex at 37° C. is −15 kCal, (iii) said oligonucleotide is complementary to a region within the target gene selected from the group consisting of 5' UTR, translational start site, translational termination site and transcription start site.

The Gibbs free energy is measured between that part of the target gene that corresponds to the oligonucleotide, that part typically being the 5'UTR, translational start site, the translational termination site, or transcription start site. In a preferred embodiment, the Gibbs Free energy of the binding of said oligonucleotide/RNA target duplex at 37° C. is ≤−20 kCal. Also preferred, the Gibbs Free energy is ≤−25 kCal. For 12-14 mer oligonucleotides, the Gibbs Free energy is preferably ≤−15 kCal, for 15-17 mer oligonucleotides, the Gibbs Free energy is preferably ≤−20 kCal, for 18-20 mer oligonucleotides, the Gibbs Free energy is preferably ≤−25 kCal, for 21-23 mer oligonucleotides, the Gibbs Free energy is ≤−30 kCal, and for 24-26 mer oligonucleotides, the Gibbs Free energy is ≤35 kCal.

Further provided by the present invention is a composition comprising an oligonucleotide, (i) wherein said oligonucleotide is about 10 to about 30 nucleotides in length, (ii) the $T_m$ of said oligonucleotide to a target gene is about 65-90° C., (iii) said oligonucleotide is complementary to a region within the target gene selected from the group consisting of 5' UTR, translational start site, an termination site and transcription start site. Preferably, the oligonucleotide has a $T_m$ of about 75-90° C. More preferably, the oligonucleotide has a $T_m$ of about 85-90° C. More preferably, the $T_m$ of said oligonucleotide to a target gene at 1M monovalent cation concentration is about 65-90° C. The Gibbs free energy is measured between that part of the target gene that corresponds to the oligonucleotide, that part typically being the 5' UTR, 3'UTR, translational start site, the translational termination site or transcription start site.

The oligonucleotide sequence can be derived from any of the genes listed in Table I, or any other gene the modulation of whose expression is likely to produce a desirable therapeutic result in influenza infection. Tables 2, 3 and 4 show representative antisense sequences that may be used in embodiments of the invention; these sequences are merely representative, and any sequence that acts as an antisense oligonucleotide and that modulates expression of a gene involved in influenza infection may be used in compositions and methods of the invention.

In some embodiments, one or more of the antisense oligonucleotides of the invention is a modified oligonucleotide. Linkage and backbone modifications have shown great promise for oligonucleotides to be used in vivo, such as 2'-O-methyls, 2'-O-allyls, locked nucleic acids and peptide nucleic acids.

In a preferred embodiment, the antisense oligonucleotides of the invention are modified to provide increased acid resistance as compared to unmodified oligonucleotide, or to provide increased resistance to endonuclease, or both. Further modifications are described below.

An antisense oligonucleotide can be constructed using chemical synthesis and enzymatic ligation reactions using procedures known in the art. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

Although the specific antisense sequences described herein (e.g., in Tables 2, 3 and 4) depict the sequences as oligonucleotides containing only deoxyribonucleotide residues, it is to be understood that the present invention also includes embodiments wherein the oligonucleotides are composed of ribonucleotide residues (e.g., by substituting uridine for thymidine, and ribosyl substituents for deoxyribosyl substituents). Moreover, it is to be understood that the present invention also includes the embodiments in which the oligonucleotides are composed of only deoxyribonucleotide residues, of only ribonucleotide residues, or of mixtures of deoxyribonucleotide and ribonucleotide residues.

In some embodiments, antisense oligonucleotides of the present invention display greater than or equal to 60, 70, 80, 90, 95, or 99 percent sequence identity to a nucleotide sequence selected from the group of SEQ ID NOS: 1-110. The oligonucleotides of the invention provide for tolerance of mismatches in sequence from that of the target gene. In some embodiments, the oligonucleotide exhibits a sequence difference of one, two, or more nucleotide units from that of the sequence selected from SEQ ID NOS: 1-110 and provides the degree of base pairing described herein to effectively suppress expression of the targeted gene. In other embodiments, the oligonucleotide exhibits up to 30% mismatches from the nucleotide sequence selected from the group of SEQ ID NOS: 1-110, and provides effective suppression of the targeted gene.

The degree of similarity between two sequences can be determined using methods well known to the art (e.g., computer programs including Fasta (Oxford Molecular Group Inc.) and BLAST (www.ncbi.nlm.nih.gov) (Altschul et al. (1997) Nucleic Acid Res. 25, 3389-3402). These methods can be employed to take into account gaps in the sequences due to deletions or insertions. Homology or sequence identity at the nucleotide or amino acid sequence level determined by BLAST (Basic Local Alignment Search Tool) analysis uses the algorithm employed by the programs blastp, blasts, blastx, tblastn and tblastx (Altschul et al. (1997) Nucleic Acids Res. 25, 3389-3402 and Karlin et al. (1990) Proc. Natl. Acad. Sci. USA 87, 2264-2268, both fully incorporated by reference) which are tailored for sequence similarity searching. The approach used by the BLAST program is to first consider similar segments, with gaps (non-contiguous) and without gaps (contiguous), between a query sequence and a database sequence, then to evaluate the statistical significance of all matches that are identified and finally to summarize only those matches which satisfy a preselected threshold of significance.

In some embodiments the antisense oligonucleotides of the invention have a Guanine:Cytosine (GC content) greater than 35 percent. In other embodiments, the GC content is greater than 40 percent. In some preferred embodiments, the GC content is greater than 45 percent.

2. Ribozymes

"Ribozyme" refers to a nucleic acid molecule which is capable of cleaving a specific nucleic acid sequence.

Ribozymes may be composed of RNA, DNA, nucleic acid analogues (e.g., phosphorothioates), or any combination of these (e.g., DNA/RNA chimerics). In some embodiments, a ribozyme refers to RNA molecules that contain anti-sense sequences for specific recognition, and an RNA-cleaving enzymatic activity.

As noted above, the present invention provides ribozymes having the ability to cleave or otherwise inhibit nucleic acid molecules which are either directly, or indirectly (e.g., they encode proteins) involved in influenza infection and host response. Several different types of ribozymes may be constructed for use within the present invention, including for example, hammerhead ribozymes (Rossi, J. J. et al., Phannac. Ther. 50:245-254, 1991) (Forster and Symons, Cell 48:211-220, 1987; Haseloff and Gerlach, Nature 328: 596-600, 1988; Walbot and Bruening, Nature 334:196, 1988; Haseloff and Gerlach, Nature 334:585, 1988; Haseloff et al., U.S. Pat. No. 5,254,678), hairpin ribozymes (Hampel et al., Nucl. Acids Res. 18:299-304, 1990, and U.S. Pat. No. 5,254,678), hepatitis delta virus ribozymes (Perrotta and Been, Biochem. 31:16, 1992), Group I intron ribozymes (Cech et al., U.S. Pat. No. 4,987,071) and RNase P ribozymes (Takada et al., Cell 35:849, 1983); (see also, WO 95/29241, entitled "Ribozymes with Product Ejection by Strand Displacement"; and WO 95/31551, entitled "Novel Enzymatic RNA Molecules."

The sequence requirement at the cleavage site for the hammerhead ribozyme is any RNA sequence consisting of NUH (where N is any of G, U, C, or A and H represents C, U, or A) can be targeted. Accordingly, the same target within the hairpin leader sequence, GUC, is useful for the hammerhead ribozyme. The additional nucleotides of the hammerhead ribozyme or hairpin ribozyme is determined by the target flanking nucleotides and the hammerhead consensus sequence (see Ruffner et al., Biochemistry 29:10695-10702, 1990).

Ribozymes, as well as DNA encoding such ribozymes and other suitable nucleic acid molecules, can be chemically synthesized using methods well known in the art for the synthesis of nucleic acid molecules (see e.g., Heidenreich et al., J FASEB 70(1):90-6, 1993; Sproat, Curr. Opin. Biotechnol. 4(1):20-28, 1993). Alternatively, commercial suppliers such as Promega, Madison, Wis., USA, provide a series of protocols suitable for the production of nucleic acid molecules such as ribozymes.

During synthesis, the ribozyme can be modified by ligation to a DNA molecule having the ability to stabilize the ribozyme and make it resistant to RNase (Rossi et al., Pharmac. Ther. 50:245-254, 1991). In another embodiment, the ribozyme can be modified to a phosphothio-analog for use in liposome delivery systems. This modification also renders the ribozyme resistant to endonuclease activity. In yet another embodiment, the ribozyme can be modified to contain propanediol linkages or to incorporate 2'-O-methylated nucleotides.

Any ribozyme that modulates expression of a gene involved in viral infection, or that is involved in host response to viral infection, e.g., the genes of Tables 1, 2, 3 and 4 may be used in the compositions and methods of the invention.

3. Interfering RNA (RNA')

In another embodiment of the present invention, double stranded nucleic acids can be used to inhibit expression of genes associated with influenza infection and host response by RNA interference. RNA interference ("RNAi") is a mechanism of post-transcriptional gene silencing in which double-stranded RNA (dsRNA) corresponding to a gene (or coding region) of interest is introduced into a cell or an organism, resulting in degradation of the corresponding mRNA. The RNAi effect persists for multiple cell divisions before gene expression is regained. RNAi is therefore an extremely powerful method for making targeted knockouts or "knockdowns" at the RNA level. RNAi has proven successful in human cells, including human embryonic kidney and HeLa cells. See, e.g., Elbashir et al. Nature May 24, 2001; 411(6836):494-8); Tuschl et al. (1999), Genes and Development 13:3191-3197; Zamore (2000), Cell 101:25-33, and U.S. Pat. No. 6,506,559, all of which are incorporated herein by reference in their entirety.

Thus, the invention further provides RNAi's that inhibit expression of influenza viral genes and animal host genes involved in response to influenza infection. In this connection, the invention provides an RNAi that modulates expression of influenza viral genes or animal host genes involved in host inflammatory or apoptotic response to viral infection. As an example, this aspect of the invention provides small (less than 50, or less than 40, or less than 30 or less than about 20 nt) dsRNA that specifically inhibits gene expression of influenza genes and host animal genes which are involved in response to influenza infection. In some embodiments, the RNAi includes: (a) double-stranded RNA of 21-25 nucleotides with overhangs of 2 nucleotdies at both 3' ends; (b) 30-52% of the G+C content of the double stranded region; and (c) A/U base pairing in positions 15-19 in sense strand; and (d) no internal repeats.

4. DNAzymes

Like RNAi, DNAzyme technology also represents an ideal choice for gene suppression. Such catalytic DNA molecules offer several advantages over ribozymes and are easier to synthesize at relatively low cost. Moreover, DNAzymes have a moderate-throughput capacity and act in a sequence-specific manner. This capacity for highly flexible binding and discrimination of nucleic acid substrates by virtue of Watson-Crick interactions enable DNAzymes to facilitate gene-type specific reactions for gene function validation with very high precision. See, e.g., Sun, L. Q., Cairns, M. J., Saravolac, E. G., Baker, A. and Gerlach, W. L. (2000) *Pharmacol. Rev.* 52(3), 325-347; and U.S. Pat. Nos. 6,617,438, 6,326,174, which are incorporated herein by reference in their entirety.

In some embodiments, the invention provides a composition that includes at least one antisense oligonucleotide targeted to an influenza viral gene and at least one antisense oligonucleotide targeted to an animal host gene involved in response to influenza infection. In some embodiments, the invention provides a composition that includes at least one antisense oligonucleotide targeted to an influenza gene (e.g. viral genes of Table 1) and at least one antisense oligonucleotide targeted to an animal host gene involved in inflammatory or apoptotic response to influenza infection. In some embodiments, the invention provides a composition that includes at least one antisense oligonucleotide targeted to an influenza viral gene wherein the sequence of the oligonucleotide is selected from SEQ ID NOS: 1-37 and at least one antisense oligonucleotide targeted to an animal host gene wherein the sequence of the oligonucleotide is selected from SEQ ID NOS: 38-110. In still other embodiments, the invention provides a composition for the suppression of expression of the influenza genes and animal host genes involved in response to influenza infection comprising two or more gene-modulating oligonucleotides, wherein at least one oligonucleotide is targeted to influenza viral genes, and at least one oligonucleotide is targeted to an animal host gene. In some embodiments the animal host gene is a gene coding for a protein selected from the group consisting of Fas, Fas-L, TACE, TNF-R1, TNF-a, Caspase-3, Rantes, IL-lb, IL-18, P38 MAPK, CXCL-1, IP-10. (Table 1). In some embodiments the composition contains one or more antisense oligonucleotides targeted to the influenza viral genes and host genes selected from the oligonucleotides shown in Tables 2, 3 and 4. In some embodiments, the compositions contain at least one antisense oligonucleotide targeted to more than one region of a single influenza viral gene, and at least one antisense oligonucleotide targeted to an animal host gene that is involved in response to influenza infection. In some embodiments, the compositions contain more than one oligonucleotide targeted to multiple influenza genes. In some embodiments, said more than one oligonucleotide is chosen from SEQ ID NOS: 1-37. In some embodiments the composition contains more than one oligonucleotide targeted to influenza genes and also contains more than one oligonucleotide targeted to animal host genes that are involved in response to influenza infection. In some embodiments, said more than one oligonucleotide targeted to influenza genes target genes shown in Table 1. In some embodiments, said more than one oligonucleotide taraeted to animal host genes involved in response to influenza infection target genes shown in Table 1. In some embodiments, said more than one oligonucleotide targeted to influenza genes is an oligonucleotide wherein the sequence is chosen from SEQ ID NOS: 1-37. In some embodiments, said more than one oligonucleotide targeted to animal host genes involved in response to influenza infection is an oligonucleotide wherein the sequence is chosen from SEQ ID NOS: 38-110.

In some embodiments, the invention provides a composition that includes at least one antisense oligonucleotide targeted to an influenza viral gene and at least one antisense oligonucleotide targeted to a gene product that modulates an animal host gene that is involved in response to influenza infection. In some embodiments, the invention provides a composition that includes at least one antisense oligonucleotide targeted to an influenza viral gene and at least one antisense oligonucleotide targeted to an animal host gene product that modulates the expression of a animal host gene that is involved in inflammatory or apoptotic response to influenza infection. In some embodiments, the invention provides a composition that includes at least one antisense oligonucleotide targeted to an influenza viral gene wherein the sequence of the oligonucleotide is selected from SEQ ID NOS: 1-37 and at least one antisense oligonucleotide targeted to a gene product that modulates the expression of a animal host gene that is involved in inflammatory or apoptotic response to influenza infection.

Any of these combinations may include a plurality of antisense oligonucleotides targeted to one or more of the target genes, e.g., combinations of oligonucleotides targeted to the 5' UTR, the 3'UTR, the start signal, coding sequences, and/or the termination signal, of one or more of the target genes.

B. Modifications of Nucleic Acids

The oligonucleotides that are employed in accordance with the present invention may be modified. An oligonucleotide that comprises at least one modification has one or more chemical modifications at the molecular level of the natural molecular structures of all or any of the nucleic acid bases, sugar moieties, internucleoside phosphate linkages, as well as molecules having added substituents, such as diamines, cholesteryl or other lipophilic groups, or a combination of modifications at these sites. For example, oligonucleotides can be end-blocked, protonated, exhibit substantial acid resistance, substantial nuclease resistance, and contain achiral internucleoside phosphate linkages and modified ribose or deoxyribose substituents.

The term “end-blocked” as used herein refers to a nucleic acid with a chemical modification at the molecular level that prevents the degradation of selected nucleotides, e.g., by exonuclease action. This chemical modification is positioned such that it protects the integral portion of the nucleic acid, for example the portion of an RNA or DNA that is chemically similar to the gene involved in the physiological condition. An end block may be a 3' end block, a 5' end block, or both. For example, a 3' end block may be at the 3'-most position of the molecule, or it may be internal to the 3' ends, provided it is 3' of the integral sequences of the nucleic acid.

The term “protonated compound” refers to a molecule of the invention that, when dissolved in water having a pH of 7 causes the pH of the solution to fall. Generally, compounds are protonated by adding protons to the reactive sites on the molecule, although other modifications of the molecule are possible, and are intended to be encompassed by this term. Such protonation can be accomplished, for example by incubating the compound in the presence of a strong acid, most preferably one with a volatile conjugate base. The term “protonation” and “acidification” as used interchangeably herein refers to the process by which protons (or positively charged hydrogen ions) are added to proton acceptor sites on a compound of the invention. The proton acceptor sites include the substituted or unsubstituted phosphates of the central group, as well as any additional proton acceptor sites on either the central group or the end blocking groups. As the pH of the solution is decreased, the number of these acceptor sites which are protonated increases, resulting in a more highly protonated compound.

Many nucleic acid backbones are not stable at low pH (e.g., pH 1-3) and experience depurination, although a number of backbones are relatively stable at pH 4-5. One aspect of the present invention reflects the recognition that certain modifications, including 2'-halide, 2'-O-alkyl, 3'-O-alkyl, and 2'-O-alkyl-n(O-alkyl) nucleic acid molecules are stable at the desired pH of 2 to 1. These modifications enhance the ability of the oligonucleotides of the pharmacological compositions of the present invention to affect a condition in vivo. Thus, the composition of the present invention may include nucleic acid molecules that are substantially acid resistant. The compositions of the present invention may also include nucleic acid molecules that are nuclease resistant. This includes nucleic acid molecules completely derivatized by 2'O-methylphosphodiesters, 2'-O-alkyl, 2'-O-alkyl-n(O-alkyl), 2'-fluoro, 2'-deoxy-erythropentofuranosyl, chimeric linkages, and any other backbone modifications, as well as other modifications, which render the nucleic acid molecules substantially resistant to endogenous nuclease activity. Additional suitable methods of rendering nucleic acid molecules nuclease resistant include, but are not limited to, covalently modifying the purine or pyrimidine bases that comprise the nucleic acid. For example, bases may be methylated, hydroxymethylated, or otherwise substituted (e.g., glycosylated) such that the nucleic acid molecules comprising the modified bases are rendered substantially nuclease resistant. Nuclease resistance also aids the oligonucleotides of the compositions of the present invention in retaining their effect in vivo.

Preferably, the oligonucleotides of the present invention remain relatively unchanged chemically upon administration to a subject and retain their activity in acidic conditions (pH less than 6.0) or in the presence of an endonuclease or exonuclease (e.g., in an in vivo setting).

The term "substantially acid resistant" as used herein refers to nucleic acid molecules that are resistant to acid degradation as compared to unmodified nucleic acid molecules. Typically, the relative acid resistance of a nucleic acid will be measured by comparing the percent degradation of a resistant nucleic acid with the percent degradation of its unmodified counterpart (i.e., a corresponding nucleic acid of the same length and sequence having a "normal" backbone and bases). A nucleic acid that is acid resistant is preferably at least one and a half times more resistant to acid degradation, more preferably at least two times more resistant, even more preferably at least five times more resistant, and most preferably at least ten times more resistant than their unmodified counterpart.

Although certain acid resistant nucleic acid molecules exhibit marked acid stability and endonuclease resistance, they are sensitive to 3' exonucleases. In order to enhance the exonuclease resistance of 2'-O-alkyl substituted nucleic acid molecules, the 3' or 5' and 3' ends of the nucleic acid are preferably attached to a chemical moiety that provides an exonuclease blocking function. For example, one or more phosphorothioate nucleotides can be placed at either end of the RNA or DNA. Additionally, one or more inverted bases can be placed on either end of the RNA or DNA, or one or more alkyl or alcohol (e.g., butanol-substituted) nucleotides or chemical groups can be placed on one or both ends. Accordingly, a preferred embodiment of the present invention is a nucleic acid comprising a nucleic acid having the following structure: A-B-C, wherein "B" is a 2'-O-alkyl or 2'-O-alkyl-n(O-alkyl) substituted RNA between about 1 and about 98 bases in length, and "A" and "C" are respective 5' and 3' end blocking groups (e.g., one or more phosphorothioate nucleotides (but typically fewer than six), inverted base linkages, or alkyl, alkenyl, alkynyl, O-alkyl, and O-alkyl-n(O-alkyl) groups or substituted nucleotides). A partial list of blocking groups includes inverted bases, dideoxynucleotides, methylphosphates, alkyl groups, aryl groups, cordycepin, cytosine arabanoside, 2'-methoxy, ethoxy nucleotides, phosphoramidates, a peptide linkage, dinitrophenyl group, 2'- or 3'-O-methyl bases with phosphorothioate linkages, 3'-O-methyl bases, fluorescein, cholesterol, biotin, acridine, rhodamine, psoralen, glyceryl, methyl phosphonates, butanol, butyl, hexanol, and 3'-O-alkyls. An enzyme-resistant butanol preferably has the structure OH—$CH_2CH_2CH_2CH_2$ (4-hydroxybutyl), which is also referred to as a C4 spacer.

The term "substantially nuclease resistant" refers to nucleic acid molecules that are resistant to nuclease degradation, as compared to naturally occurring or unmodified nucleic acid molecules. Modified oligonucleotides of the invention are at least 1.25 times more resistant to nuclease degradation than an unmodified nucleic acid having the same sequence and number of nucleotides, more preferably at least 2 times more resistant, even more preferably at least 5 times more resistant, and most preferably at least 10 times more resistant than their unmodified counterpart. Such substantially nuclease resistant nucleic acid molecules include, but are not limited to, nucleic acid molecules with modified backbones such as ethylphosphotriesters, 2'-O-methylphosphorothioates, 2'-O-methyl-p-ethoxy ribonucleotides, 2'-O-alkyls, 2'-O-alkyl-n(O-alkyl), 2'-fluoros, 2'-deoxy-erythropentofuranosyls, 2'-O-methyl ribonucleosides, 2'-O-(ethoxy)methyl ribonucleosides, 3'-O-methylribonucleosides, inverted bases (e.g., inverted T's), or chimeric versions of these backbones.

The modified oligonucleotide includes RNA or DNA comprising modifications to the sugar moieties such as 2'-substituted or 3'-substituted ribonucleotides, or deoxyribonucleotide monomers, any of which are connected together via internucleoside linkages. Modified RNA or DNA may also be comprised of PNA or morpholino modified backbones where specificity of the sequence is maintained.

The ribose groups and the internucleoside linkages link the bases in a nucleic acid and are referred to as the nucleic acid backbone. A modified backbone includes modifications to the chemical linkage between nucleotides, as well as other modifications that may be used to enhance stability and affinity, such as modifications to the sugar structure. For example, an L-anomer of deoxyribose may be used, where the base is inverted with respect to the natural D-anomer. In one embodiment, the 2'-OH of the sugar group may be altered to 2'-halogen, 2'-O-alkyl or 2'-O-alkyl-n(O-alkyl), which provides resistance to degradation without compromising affinity. Other suitable modified backbones incorporating internucleotide linkages may include phosphodiesters, phosphothioates, and the like. Combinations of backbone and ribose modifications may be used, for example: 2'O-methyl-phosphodiesters, 2'O-alkyl-phosphodiesters, 2'-O-ethyl-phosphodiesters, 2'-O-propyl-phosphodiesters, 2'-O-butyl-phosphodiesters, 2'-O-alkyl-n(O-alkyl)-phosphodiesters, 2'-methoxyethoxy-phosphodiesters, 2'-fluoro-phosphodiesters, 2'-deoxy-erythropentofuranosyl, 3'-O-methyl, p-isopropyl oligonucleotides, 2'-O$(CH_2CH_2)_xCH_3$, and/or butyne linkages. An oligonucleotide may have combinations of such modified backbones, may be completely modified, or may comprise all or some linkages being phosphodiester linkages.

Preferred internucleoside linkages on the modified oligonucleotide are achiral. The term "achiral" as used herein, refers to a molecule that is superimposable with its mirror image, whereas the term "chiral" refers to a molecule that is not superimposable with its mirror image. Oligonucleotides containing achiral 5' to 3' internucleoside phosphate linkages have internucleotide linkages which are achiral (i.e., no stereochemistry). The achiral oligonucleotides preferably contain at least about three to eight contiguous achiral internucleoside linkages, more preferably, nine to ten contiguous achiral internucleoside linkages, even more preferably, eleven to twelve contiguous achiral internucleoside linkages, and most preferably, is completely comprised of achiral internucleoside linkages through the entire contiguous sequence. In another embodiment, the achiral internucleoside linkages are interspersed with chiral internucleoside linkages (e.g., two contiguous achiral linkages followed by one chiral linkage followed by two contiguous achiral linkages; three contiguous achiral linkages followed by one chiral linkage; four contiguous achiral linkages followed by two achiral linkages, etc.). Examples of achiral internucleoside linkages include, but are not limited to, phosphodiester and diphosphorothioate linkages. Achiral RNA and DNA linkages in the backbone are routinely generated during automated synthesis of oligonucleotides if the final structure is a symmetrical molecule (i.e., a phosphate with the same atom attached to both sides).

The internucleoside phosphate linkages can be phosphodiester, or 3' to 3', 5' to 2' or 5' to 5' linkages, and combinations of such similar linkages (to produce mixed backbone modified RNA or DNA). The modifications can be internal (single or repeated) or at the end(s) of the RNA or DNA molecule. These modifications can include additions to the nucleic acid molecule, such as cholesteryl, diamine compounds with varying numbers of carbon residues between amino groups and terminal ribose, and deoxyribose or phosphate modifications which cleave or cross-link to the opposite chains or to associated enzymes or other proteins. Electrophilic groups such as ribose-dialdehyde could covalently link with an epsilon amino group of the lysyl-residue of such a protein. A nucleophilic group such as n-ethylmaleimide tethered to an RNA or DNA could covalently attach to the 5' end of an niRNA or to another electrophilic site.

Efficacy of a particular composition may be determined by means known in the art. These include in vitro and in vivo methods, such as, e.g., analysis of expression in cell culture contacted with the compositions, analysis of expression and/or phenotypic characteristics and/or physiological characteristics in an in vivo model, and clinical trials. In vivo models include established animal models for influenza infection. For influenza infection regulating compositions, model systems such as those provided in the Examples may be used.

C. Compositions

Compositions of the present invention include compositions that contain a single gene-expression modulating oligonucleotide, or, in some preferred embodiments, combinations of gene-expression modulating oligonucleotides. The oligonucleotides are directed at genes involved in influenza infection. Compositions may include only one type of oligonucleotide, e.g., only antisense oligonucleotides. Compositions may include more than one type (e.g., any combination of antisense oligonucleotides, RNAi, microRNA, ribozymes and/or DNAzymes). Compositions may include multiple oligonucleotides directed against multiple areas of a single gene. For example, in some embodiments, the invention provides combinations of oligonucleotides, e.g., antisense oligonucleotides, that target the 5' untranslated region (UTR), the 3'UTR, the start, and/or the termination signal of an mRNA derived from a gene, or the transcription start site of a gene. Compositions may include multiple oligonucleotides directed against more than one gene. Compositions may include multiple oligonucleotides directed against multiple areas of multiple genes.

The compositions of the invention typically include more than about one, two, three, four, five, six, seven, eight, nine, 10, 15, 20, 30, 40, 50, 75, or 100 different oligonucleotides. Preferably, the compositions of the invention include about two to about 20 different oligonucleotides. More preferably, the compositions of the invention include about two to about 15 different oligonucleotides, and most preferably, the compositions of the invention include about two to about 10 different oligonucleotides; or alternatively, compositions of the invention include about two to about eight different oligonucleotides or about two to about six different oligonucleotides. In some embodiment, compositions of the invention include about two to about four different oligonucleotides. Thus, in some embodiments, the invention provides combinations of two or more oligonucleotides targeted to suppressing expression of two or more different genes involved in influenza infection. Exemplary genes to which the antisense oligonucleotides may be directed are listed in Table 1.

In some embodiments, the invention provides one or more antisense oligonucleotides to an influenza gene. In some embodiments, the invention provides a combination of antisense oligonucleotides to art influenza gene that includes at least two different antisense oligonucleotides to an influenza gene. In some embodiments, the influenza gene is selected from the group consisting of different influenza viral genes. In some embodiments, the invention provides a combination of antisense oligonucleotides to different parts of the influenza gene transcript, including at least two antisense oligonucleotides targeted to portions of the transcript selected from the group consisting of the 5' UTR, the 3' UTR, the translation start, the termination signal and the transcription start site. In some embodiments, the invention provides a combination of antisense oligonucleotides to an influenza gene, including at least two antisense oligonucleotides selected from the group consisting of SEQ ID NOS: 1-110.

In some embodiments, the invention provides a composition that includes at least one antisense oligonucleotide targeted to an influenza gene and at least one antisense oligonucleotide targeted to at least one host gene selected from those listed in Table 1. Some embodiments provide combinations of antisense oligonucleotides targeted to an influenza gene and to two or more other host genes listed in Table 1. In some embodiments, the invention provides a composition that includes at least one antisense oligonucleotide targeted to the influenza gene and at least one antisense oligonucleotide targeted to at least one of Fas, Fas-L, TACE, TNF-R1, TNF-α, Caspase-3, Rantes. IL-1b, IL-18, P38 MARK, CXCL-1 and IP-10.

In some embodiments, the invention provides a composition that includes at least one antisense oligonucleotide targeted to influenza viral genes and at least one antisense oligonucleotide targeted to the host genes wherein the sequence of the oligonucleotide is selected from SEQ ID NOS: 1-110.

Any of these combinations may include a plurality of antisense oligonucleotides targeted to one or more of the target genes, e.g., combinations of oligonucleotides targeted to the 5' UTR, the 3'UTR, the start signal, the termination signal, and/or the transcription start site of one or more of the target genes.

D. Pharmaceutical and Homeopathic Compositions

The invention further provides pharmaceutical and homeopathic compositions.

Pharmaceutical compositions. The present invention includes pharmaceutical compositions comprising at least about one oligonucleotide as described herein. In some embodiments, the invention provides pharmaceutical compositions that include at least two, three, four, five, six, seven, eight, nine, 10, 15, 20, 30, 40, 50, 75, or 100 different oligonucleotides, as described herein. In some embodiments, one or more of the oligonucleotides is a modified oligonucleotide. In some embodiments, the pharmaceutical composition contains one or more antisense oligonucleotides, any or all of which may be modified as described herein. The pharmaceutical compositions further comprise a pharmaceutically suitable excipient.

As used herein, the term "pharmaceutical composition" refers to a therapeutic composition that is used to treat a particular disease or pathological disorder that is suitable for parenteral, oral or topical administration in humans and animals.

The compositions containing the oligonucleotides of the invention in an admixture with a pharmaceutically acceptable carrier can be prepared according to known techniques. The excipient may take a wide variety of forms depending on the form of preparation desired for administration, e.g., intravenous, oral, topical, aerosol (for topical or inhalation therapy), suppository, parenteral, or spinal injection. The excipient may contain any number of carriers. In addition, the composition may contain stabilizers, preservatives, and other ingredients, preferably in amounts from about 0.5 to 2.0 percent by weight, provided they do not adversely affect the ability of the pharmacological composition to treat the physiological condition. Formulations of the compositions of the invention may comprise liposomes, nanoparticles, suspensions, solutions, aerosolized solutions and particles, transdermal delivery systems, or solids. It is well within the skill of one in the art to determine an appropriate mode of administration and to select an appropriate delivery system.

Administration of the composition will introduce the modified oligonucleotides to the individual in a diluted amount. Exemplary unit dosages for oral or topical administration may be more than about 0.01, 0.05, 0.1, 0.5, 1, or 5 mg/kg, and/or less than about 10, 5, 1, 0.5, 0.1, or 0.05 mg/kg. Exemplary unit dosage ranges may be between about 0.01 mg/kg and 10 mg/kg, or between about 0.010 mg/kg and 1.0 mg/kg, or between about 0.10 mg/kg and 1.0 mg/kg for a composition that contains a single oligonucleotide. In some embodiments, the oligonucleotide compositions of the present invention are administered at unit dosages of about 0.01 to about 100 ug per kg of body weight, or about 0.1 to about 100 ug per kg of body weight, or about 0.1 to about 10 ug per kg of body weight, or about 1 to about 10 ug per kg of body weight, or about 1 to about 5 ug per kg of body weight. When more than one oligonucleotide is present in the composition, dosages of each oligonucleotide may be in the latter ranges, or dosage of one or more of the oligonucleotides may be decreased, based on the expected overall effect of the combination. In some embodiments, unit dosages per single oligonucleotide are at or below 100 ug per kg of body weight, or at or below 10 ug per kg of body weight, or at or below 1 ug per kg of body weight, or at or below 0.1 ug per kg of body weight, or at or below 0.01 ug per kg of body weight.

When orally administered, one dosage unit may be administered once every 10, 9, 8, 7, 6, 5, 4, 3, 2, or one day, or 1, 2, 3, 4, 5, 6, 7, 8, 9, 10, or more than 10 times per day until relief is achieved or until the symptoms disappear or are satisfactorily attenuated. In some embodiments, one dosage unit is administered about once to about four times per day. In some embodiments, a patient is instructed to orally take two to three dosage units per day. The dosage unit may be placed under the tongue of the patient or simply swallowed for such oral administration.

The pharmaceutical compositions of the present invention may be formulated for administration to humans and animals in liquid form, or in tablets, pills, granules, powders, or in ointments, creams, injectables, or suppositories. Ointments and creams are impregnated with a low liquid potency or, sometimes, mother tinctures and are generally prescribed as specific remedies. Liquid compositions may be supplied in amber glass dropper bottles to protect them from light.

In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs, and solutions); or carriers such as starches, sugars, diluents, granulating agents, lubricants, binders, disintegrating agents and the like in the case of oral solid preparations (such as, for example, powders, capsules and tablets).

For administration by injection, preparations may comprise an aqueous solution of a water soluble, or solubilized, and pharmacologically acceptable form of the nucleic acid in an appropriate liquid, e.g., water or saline solution. Injectable suspensions may also be prepared using appropriate liquid carriers, suspending agents, agents for adjusting the isotonicity, preserving agents, and the like. Actual methods for preparing administrable pharmacological compositions and adjustments necessary for administration to subjects will be known or apparent to those skilled in the art.

For topical administration, the carrier may take a wide variety of forms depending on the preparation, which may be a cream, dressing, gel, lotion, ointment, or liquid. A surfactant can be included in the composition to provide deeper penetration of the ingredients. Although natural surfactants are preferred, others such as isopropyl myristate can be used.

Aerosols are prepared by dissolving or suspending the nucleic acid in a propellant such as ethyl alcohol or in propellant and solvent phases. The pharmaceutical compositions for topical or aerosol form will generally contain from about 0.001 percent by weight (of the nucleic acid) to about 40 percent by weight, preferably about 0.02 percent to about 10 percent by weight, and more preferably about 0.05 percent to about 5 percent by weight depending on the particular form employed. Suppositories are prepared by mixing the nucleic acid with a lipid vehicle such as theobroma oil, cacao butter, glycerin, gelatin, or polyoxyethylene glycols.

The nucleic acid molecule(s) may be combined with a lipid, cationic lipid, or anionic lipid and the active agent delivered via a nucleic acid/lipid emulsion, or a liposomal suspension. By assembling nucleic acid molecules into lipid-associated structures, the nucleic acid molecules may exhibit an increased half-life in vivo. Examples of suitable anionic lipids for use with RNA or DNA include, but are not limited to, cardiolipin, dimyristoyl, dipalmitoyl, or dioleoyl phosphatidyl choline or phosphatidyl glycerol, palmitoyloleoyl phosphatidyl choline or phosphatidyl glycerol, phosphatidic acid, lysophosphatidic acid, phosphatidyl serine, phosphatidyl inositol, and anionic forms of cholesterol.

Homeopathic compositions. In some embodiments, the invention provides homeopathic compositions. Homeopathic compositions may be made by methods known in the art. One exemplary method of making a homeopathic composition comprises (i) triturating solid oligonucleotide of the invention in a 1/9 ratio with lactose to produce a 1X solid and (ii) repeating the process until the desired attenuation is achieved. In a related vein, a method of making a homeopathic composition comprising (i) dissolving 1 part oligonucleotide of the invention by weight in liquid to produce ten volumes of liquid attenuation labeled 1X and optionally (ii) mixing 1 ml of the 1X attenuation with 9 ml of diluent to produce a lower concentration, is also addressed.

In some embodiments, the invention includes homeopathic compositions containing modified oligonucleotides. Any oligonucleotide or combination of oligonucleotides described herein may be used in the homeopathic compositions. In one embodiment, tablets for homeopathic use are preferably produced as placebo tablets that are then medicated by dripping or spraying liquid potencies onto the tablets in such a manner as to ensure a coefficient of impregnation of almost 100 percent. The placebo tablets are preferably formed by compression. Pills or granules are preferably spherical in shape, of about 4 millimeters diameter and 3 to 5 centigrams in weight. They are preferably prepared (from pure lactose) and medicated in the same manner as tablets. For example, solid oligonucleotides or combinations of oligonucleotides can be triturated (i.e., ground up) in a 1/9 ratio with lactose (1 gram of oligonucleotide+9 grams of lactose) to produce a 1X solid. The process is repeated (1 gram of that material plus 9 grams of lactose) until the desired attenuation is achieved.

For homeopathic compositions, the excipient may contain any number of carriers, and preferably homeopathic carriers, e.g., homeopathic agents that may increase the efficacy of the homeopathic composition or help to alleviate symptoms associated with a physiological condition. For example, oligonucleotides or combinations of oligonucleotides can be dissolved in a liquid 1 part by weight to produce a tenfold volume liquid attenuation labeled 1X. To produce lower dilutions 1 ml of the 1X attenuation is used (mixed thoroughly) with 9 ml of diluent to produce 2X. This process is repeated until the desired attenuation is achieved. A homeopathic carrier solution such as that described in U.S. Pat. No. 5,603,915 may be used for increasing the efficacy of the homeopathic agent. This carrier solution is sequentially subjected to an alternating current electrical treatment and a direct current electrical treatment, after which additional ingredients such as seawater, brain hormones, and biologically active enzymes are added. The electrical treatment of the carrier, along with the addition of homeopathically active substances, can be used to increase the efficacy of the homeopathic composition.

Alternatively, an electromagnetic carrier, such as described in U.S. Pat. No. 5,830,140 may be employed. For homeopathic preparations for example, oligonucleotides or combinations of oligonucleotides can be dissolved in a liquid 1 part by weight to produce a ten volumes of liquid attenuation labeled 1X. To produce lower dilutions 1 ml of the 1X attenuation is used (mixed thoroughly) with 9 ml of diluent to produce 2X. This process is repeated until the desired attenuation is achieved. Typical homeopathic unit doses are given in Table 6.

II. Methods of the Invention

The invention further provides methods of treatment using the compositions of the invention. Methods include methods of modulating gene expression in cells by contacting cells with compositions of the invention. Methods also include methods of treatment and prevention of influenza infection.

The compositions and methods of the invention target individual genes as well as, preferably, combinations of genes involved in influenza infection. By employing combination compositions and therapies, drug resistance by potential viral escape mutants may be avoided, and multiple pathways may be targeted simultaneously, leading to greater therapeutic effect than when single genes are targeted.

Further, the use of modified oligonucleotides targeting the group of viral genes as shown in Table 1 or the use of the sequences of Table 2 for the design of oligonucleotides of according to the invention, permits rapid development of specifically targeted therapeutics of both current coexisting influenza strains and newly emerged strains. This is possible because the RNAS disclosed herein have homology with multiple strains of influenza. For example, the RNA sequence of NS-2 (target sequence at position 2 in the NS1 gene, SEQ ID NO: 14) has 100% homology with at least 21 different strains of influenza.

However, the compositions of the invention also provide for oligonucleotides which contain one, two or more mismatches with the sequences of Table 2, in order to provide effective suppression of the expression of variant forms of influenza genes. Comparison of sequence searches using software search programs as described herein, allows identification of variations from the sequences of Table 2 at selected positions within a relatively conserved region. Oligonucleotides are then synthesized to incorporate these variations for use in compositions of the invention.

Two examples are shown in Table 7 and 8.

For NS 526, the oligonucleotide sequence is: CCT CAg CAg TAT gTC CTg (SEQ ID NO. 20). Variant 1, (SEQ ID NO 111, Table 7) differing at the sixth residue, substituting C for g, and Variant 2 (SEQ ID NO 112, Table 7), differing at the sixth nucleotide, substituting T for g, confer effective binding against the majority of predominate viral strains. A preferred embodiment uses a combination of NS 526, Variant 1 and Variant 2 to effectively suppress symptoms of influenza across a wider range of influenza strains.

For NS 705, which has a sequence of TCT TCA AAC TTC TgA CCT (Table O, SEQ ID NO. 21), two variations can be designed, which will create effective suppression of this region of the NS gene across the majority of known strains. Variation 3 (SEQ ID NO 113, Table 8), substitutes T for C at the twelfth nucleotide of the sequence and Variation 4 (SEQ ID NO 114, Table 8) substitutes G for A at sixth nucleotide of the sequence. Variation 3 represents the major variant between strains, and adding Variation 4 along with it to NS 705 to form a composition containing three different oligonucleotides with these three sequences, which effectively suppresses that region of the NS gene across a wide variety of influenza strains.

In some embodiments of the invention, these mixtures of NS sequences are further combined with other oligonucleotides which target other influenza genes or target animal host genes involved in response to influenza infection. As described above for two sequences NS 526 and NS 705, the same approach can be extended to any of SEQ ID NO: 1-110, to obtain multi-strain efficacy.

Lower toxicity, if any, may be obtained by the use of combination therapies due to the potentially lower amounts of each particular gene modulator being used. In addition, combinations of inhibitors, and combinations of targets in single genes are encompassed by the methods of the invention. In general, gene modulators used in compositions and methods of the invention are targeted at genes whose expression is desired to be inhibited; however, in some cases, some of the gene modulators used in embodiments of the invention may result in an increase in expression.

The invention also encompasses modified oligonucleotides for use in gene modulation, where the modified oligonucleotides are typically more stable and resistant to degradation than natural oligonucleotides; the modified oligonucleotides of the present invention are less toxic than many presently-used modifications (e.g., S-oligonucleotides), thus allowing dosages to be higher without adverse side effects.

Influenza virus is transmitted mainly via aerosol through respiratory tract, although some other routes are also responsible for the influenza infection, such as mouth and eye. Avian H5N1 influenza A virus could be transmitted directly from poultry to humans with an overall case-fatality rate of 33%. Affected patients had a primary viral pneumonia complicated by acute respiratory distress, multiple organ dysfunction and haemophagocytosis.

The genome of influenza virus consists of eight fragments, each of which codes for different viral genes:

RNA polymerase genes (PB1, PB2 and PA)—These three genes are located in the fragment 2, 1 and 3 respectively. The products of these genes form a complex that directs the viral replication and transcription.

Hemagglutin gene (HA)—This gene is located in the fragment 4 coding for proteins responsible for the viral binding and entering to the host cells.

Matrix gene (M)—This gene codes for matrix proteins M1 and M2.

Nuclear protein gene (NP)—This gene is located in the fragment 5 coding for the viral nuclear protein responsible for viral RNA synthesis.

Neuroaminase gene (NA)—This gene is located in the fragment 6 coding for an enzyme participating in the viron release.

Non-structure gene (NS)—NS gene is located in the fragment 8 coding for two gene products, NS1 and NS2. NS proteins are responsible for regulation of the viral replication and transcription, as well as the interactions between the virus and host cells.

Replication of influenza viruses in the respiratory tract leads to cell damage and liberation of cytokines and chemokines, which lead to inflammation and respiratory symptoms. The mechanisms involved in cell death and cytokine production are becoming better understood and appear to be intrinsically linked. It has been suggested that the influenza induced apoptosis is beneficial to the viral release and responsible for the lung tissue injury. Several host gene products are key regulatory components in many influenza-induced apoptotic pathways, such as. Caspase 3, Fas, Fas-L, TACE, TNF-R1, Rantes and TNF-α. Suppression of the expression of these genes in the infected cells may provide a therapeutic effect on the influenza infection and associated symptoms.

Influenza virus infection of epithelial cells and phagocytes induce apoptosis. This not only leads to direct damage of such cells but it becoming apparent that such cells produce pro-inflammatory cytokines. This inflammatory response directly damages the host as the inflammatory cells release pyrogenic cytokines that not only induce fever but all the constitutional signs and symptoms of influenza. As in the infection by the subtype of H5N1 strain, overproduction of pro-inflammatory cytokines showed to be extremely serious and even fatal. These cytokines and cellular factors include IL 1b, CXCL-1, IP-10, IL18, NF-kB and P38MAPK.

The invention provides for the design of microRNAs directed against conserved regions of each viral gene. Three to five microRNAs were designed against each viral gene, i.e., HA, PB1, PB2, PA, NP, NS, HA, and M. The schematic representation of the location and function descriptor is shown in FIG. 1. A variety of microRNAs were also designed against animal host genes involved in inflammation. The invention provides for the design of microRNAs designed against animal host genes involved in apoptosis.

The present invention also provides methods and compositions for the treatment of humans and animals.

The term "treating" and its grammatical equivalents as used herein include achieving a therapeutic benefit and/or a prophylactic benefit. By therapeutic benefit is meant eradication, amelioration, or prevention of the underlying disorder being treated.

Thus, the method of treating of the present invention covers any treatment of symptoms associated with influenza infection in an animal, in some preferred embodiments, a bird; in some preferred embodiments, a mammal; in some particularly preferred embodiments, a human; and includes:

(a) preventing symptoms of a disorder from occurring in a subject that may be the elderly, children or those with pre-existing medical conditions (b) inhibiting symptoms of influenza infection (i.e., arresting its development); or (c) relieving symptoms of influenza infection (i.e., ameliorating and/or causing regression of the condition).

One of ordinary skill will appreciate that, from a medical practitioner's or patient's perspective, virtually any alleviation or prevention of an undesirable symptom would be desirable.

The dosages of the oligonucleotide composition in animals will depend on the disease or condition being, treated, the route of administration, the physical characteristics of the animal being treated, and whether the treatment is allopathic or homeopathic. The dosages of the oligonucleotide composition in animals will depend on whether the treatment is therapeutic or prophylactic.

The compositions of the present invention are formulated to contain a "allopathically effective" or "homeopathically effective amount of one or more nucleic acid molecules. As used herein, the term "allopathically effective" amount is meant to refer to an amount of an oligonucleotide composition that is non-toxic and greater than the minimum amount necessary to produce a desired physiological effect. As used herein, the term "homeopathically effective" amount is meant to refer to an amount of a oligonucleotide composition that is non-toxic and is the lowest amount necessary to provide a desired physiological effect. A homeopathic effect, in accordance with the present invention, is achieved by a dose of modified nucleic acid that will be effective in treating (i.e., relieving, ameliorating, or preventing) symptoms of a particular condition or disease. Such treatment may be prophylactic in nature (i.e., completely or partially preventing the future occurrence of a symptom) and/or it may be therapeutic in nature (1.e., providing a partial or complete cessation or amelioration of a symptom).

Accordingly, in embodiments wherein the treatment utilizes allopathically effective amounts of compositions, the oligonucleotide compositions of the present invention may be administered at a unit dosage more than about 0.01, 0.05, 0.1, 0.5, I, or 5 mg/kg, and/or less than about 10, 5, 1, 0.5, 0.1, or 0.05 mg/kg. Exemplary unit dosage ranges may be between about 0.01 mg/kg and 10 mg/kg, or between about 0.010 mg/kg and 1.0 mg/kg, or between about 0.10 mg/kg and 1.0 mg/kg for a composition that contains a single oligonucleotide. In some embodiments, the oligonucleotide compositions of the present invention are administered at unit dosages of about 0.01 to about 100 ug per kg of body weight, or about 0.1 to about 100 ug per kg of body weight, or about 0.1 to about 10 ug per kg of body weight, or about 1 to about 10 ug per kg of body weight, or about 1 to about 5 ug per kg of body weight. When more than one oligonucleotide is present in the composition, dosages of each oligonucleotide may be in the latter ranges, or dosage of one or more of the oligonucleotides may be decreased, based on the expected overall effect of the combination. In some embodiments, unit dosages per single oligonucleotide are at or below 100 ug per kg of body weight, or at or below 10 ug per kg of body weight, or at or below 1 ug per kg of body weight, or at or below 0.1 ug per kg of body weight, or at or below 0.01 ug per kg of body weight.

When orally administered, one dosage unit may be administered once every 10, 9, 8, 7, 6, 5, 4, 3, 2, or one day, or 1, 2, 3, 4, 5, 6, 7, 8, 9, 10, or more than 10 times per day until relief is achieved or until the symptoms disappear or are satisfactorily attenuated. In some embodiments, one dosage unit is administered about once to about four times per day. In some embodiments, a patient is instructed to orally take two to three dosage units per day. The dosage unit may be placed under the tongue of the patient or simply swallowed for such oral administration.

Modified oligonucleotides as described herein, e.g., achiral oligonucleotides of naturally occurring phosphodiester DNA and RNA linkages with 3' nuclease protection and sometimes also 5' nuclease protection, are not toxic, allowing a wide range of dosages to be possible with compositions of the present invention. For example, the dietary supplement recommendation for nucleic acids is 0.5 to 2.0 gm/day.

Metabolites are naturally occurring compounds that occur in foods and as byproducts of cell catabolism. Furthermore, such compounds do not elicit an immune response. Accordingly, in some embodiments, dosages range from about 10 ug to 100 mg/kg/per day or 0.01 gm to 10 gm/kg per day, or 0.01 to 1 gm/kg/day, or 0.01 to 0.1 gm/kg/day.

Homeopathic compositions typically employ substantially less nucleic acid than is employed in allopathic or nutritional compositions. Exemplary dosages to be employed in accordance with the present invention are described in Table 6. Furthermore, for homeopathic use, the oligonucleotide compositions of the present invention can be combined with any homeopathic drug and still elicit a therapeutic effect.

Oligonucleotide compositions of the present invention may be co-administered with other active pharmaceutical agents depending on the condition being treated. Pharmaceutical agents useful in the treatment of influenza infection, their optimal dosages and routes of administration, are known in the art. Co-administration can include simultaneous administration of the two agents in the same dosage form, simultaneous administration in separate dosage forms, and separate administration.

The oligonucleotide composition can be administered by injection, topically, orally, transdermally, or rectally. Preferably, the composition is administered orally. The oral form in which the oligonucleotide is administered can include powder, tablet, capsule, solution, or emulsion. The effective amount can be administered in a single dose or in a series of doses separated by appropriate time intervals, such as hours.

In some embodiments, one or more of the oligonucleotides comprises at least one modification according to the present invention. A preferred modification is the incorporation of at least about three to eight contiguous achiral internucleoside phosphate linkages into the oligonucleotide backbone, or at least about nine to ten continuous achiral internucleoside phosphate linkages or at least about eleven to fifteen achiral internucleoside phosphate linkages, or the entire oligonucleotide contains achiral internucleoside phosphate linkages. In some embodiments the oligonucleotide is 3' end-blocked.

The methods of the present invention can be used to treat symptoms associated with influenza infection. Table 5 lists the target genes or combinations of target genes that are preferably employed in preparation of gene-modulating compositions of use in remedies for the treatment of various symptoms and conditions. In Table 5, the use of a combination of target genes is denoted by a "/" (for example, "A/B/C" denotes the combination of target genes A, B and C); where two or more different combinations are preferred, each such combination is presented on a separate line. The gene-modulating compositions targeted at the genes are usually used in a 1:1:1 ratio, but this can vary. Any other ratio of compositions may also be used in combinations, depending on the condition to be treated, the state of the subject, and other factors that are known in the art.

Preferably, animals, e.g., mammals, are treated using compositions of the present invention having agents with compositions containing nucleic acid molecules having a sequence appropriate for the particular animal. Targeted species include, but are not limited to birds, and mammals (especially chickens, pigs, goats, sheep, cows, dogs, horses, cats, and most preferably, humans). One of skill in the art can determine if a particular therapeutic course of treatment is successful by several methods known to those of skill in the art.

TABLE 1

Exemplary genes

| Target genes | Accession number |
|---|---|
| **Influenza viral genes** | |
| PA | A/PR/8/34 |
| PB1 | A/PR/8/34 |
| PB2 | A/PR/8/34 |
| NS1 | A/PR/8/34 |
| NA | A/PR/8/34 |
| HA | A/PR/8/34 |
| NP | A/PR/8/34 |
| M | A/PR/8/34 |
| **Human apoptotic genes** | |
| Fas | NM000043 |
| Fas-L | NM000639 |
| TACE | NM003183 |
| TNF-R1 | NM001065 |
| TNF-α | NM000594 |
| Caspase-3 | NM004346 |
| **Human cytokines and cellular factors** | |
| CXCL1 | NM001511 |
| IL1b | NM000576 |
| IL18 | NM001562 |
| IP-10 | NM001565 |
| RANTES | M21121 |
| P38MAPK | NM001315 |
| NF-kB | M62399&L19067 |
| **Avian genes** | |
| Caspase 3 | AF083029 |
| Fas | AF296874 |
| Fas-L | AF296875 |
| TNF-α | AY765397 |
| TACE | NM001008682 |

TABLE 2

Exemplary oligonucleotides targeted at influenza genes

| Influenza genes | Antisense oligonucleotides | Seq ID |
|---|---|---|
| PA | 5'-CAU UUC gAA UCA gUA CCU gC-3' | 1 |
| | 5'-UCC CUU CUC CUU CGU gAC-3' | 2 |
| | 5'-CAG CAC UgC CAU AAC UAU-3' | 3 |
| | 5'-ggg TTg AAg CAT TgT CgC-3' | 4 |
| | 5-CCT CCA ggT gAg TgC ATA-3' | 5 |
| PB1 | 5'-CAT TCA AAT ggT TTg CCT-3' | 6 |
| | 5'-CAA TTg CTC gCC TCT TCA-3' | 7 |
| | 5'-CCC Tag ACA CCA Tgg CCT-3' | 8 |
| | 5'-ggA CAA gCT AAA ITC ACT-3' | 9 |
| PB2 | 5'-TCT CTC CAT ATT gAA TAT-3' | 10 |
| | 5'-TAC AgC Tag ggg AgA CAC-3' | 11 |
| | 5'-TTC Tgg CAg CgA TgA TCA-3' | 12 |
| | 5'-ACA CTA ATT gAT ggC CAT-3' | 13 |
| NS | 5'-UUg UCA CCC UgC UUU UgC-3' | 14 |
| | 5'-CAC AgU gUU Ugg AUC CAU-3' | 15 |
| | 5'-CCU CAg CAg UAU gUC CUg-3' | 16 |
| | 5'-UCU UCA AAC UUC UgA CCU-3' | 17 |
| | 5'-TTg TCA CCC TgC TTT T-3' | 18 |
| | 5'-TTg TCA CCC TgC IT-3' | 19 |
| | 5'-CCT CAT CAg TAT gTC CTg-3' | 20 |
| | 5'-TCT TCA AAC TTC TgA CCT-3' | 21 |
| NP | 5'-gAC gCC ATg ATg TTg ATg-3' | 22 |
| | 5'-CCC CTr TAC 'TgC TgC ACC-3' | 23 |
| | 5'-TgC TCT TTg TgC TgC TgT-3' | 24 |
| | 5'-AAg ACT CCC CgC CCC Tgg-3' | 25 |

TABLE 2 -continued

| Exemplary oligonucleotides targeted at influenza genes | | |
|---|---|---|
| Influenza genes | Antisense oligonucleotides | Seq ID |
| HA | 5'-CTC CAT TIT gAC AgA TTg AAC-3' | 26 |
| | 5'-gTC AAC CTg CTC TgT CgA 3 | 27 |
| | 5'-AAA ICC CCT ggg 'FAA CAg-3' | 28 |
| | 5'-TgA ATC CCC CAC AgT ACC-3' | 29 |
| NA | 5'-TCA TTT TgA ACT CCT gCT-3' | 30 |
| | 5'-ACA gAT TgA TCC gAT ggT-3' | 31 |

TABLE 2 -continued

| Exemplary oligonucleotides targeted at influenza genes | | |
|---|---|---|
| Influenza genes | Antisense oligonucleotides | Seq ID |
| | 5'-CCC CCT Tgg AAC CgA TCC-3' | 32 |
| | 5'-gTA CTT CAC TAC AgC CAC-3' | 33 |
| M1, 2 | 5'-Cgg TTA gAA gAC 'TCA TCT-3' | 34 |
| | 5'-TgA ggg ggC CTg ACg ggA-3' | 35 |
| | 5'-CgT CTA CgC TgC AgT CCT-3' | 36 |
| | 5'-gTA ggC CTg CAA ATT TTC-3' | 37 |

TABLE 3

| Exemplary oligonucleotides targeted at animal host genes involved in response to influenza infection | | | |
|---|---|---|---|
| Host genes | Accession# | Antisense oligonucleotides | Seq ID |
| Human CXCL-1 | NM_001511 | 5'-gCA gCg Cgg gCC ATg ggg-3' | 38 |
| | | 5'-ggT CAg TTg gAT TTg TCA-3' | 39 |
| Human IL-1b | NM_000576 | 5'-gCC ATg gCT gCT TCA gAC-3' | 40 |
| | | 5'-ggT ACA gCT CTC TTT Agg-3' | 41 |
| Human IP-10 | NM_001565 | 5'-TTg ATT CAT ggT gCT gAg-3' | 42 |
| | | 5'-TCC CCT CTg gTT TTA Agg-3' | 43 |
| Human IL-18 | NM_001562 | 5'-CAg CAg CCA TCT TTA TTC-3' | 44 |
| | | 5'-AgC Tag TCT TCg TTT TgA-3' | 45 |
| | | 5'-CTCTTTCgTTCCCggTgg-3' | 46 |
| Human IL-6 | NM000600 | 5'-AAGgAgTTCATAgCTggg-3' | 47 |
| | | 5'-CCATgCTACATTTgCCgA-3' | 48 |
| | | 5'-gAACAgTTCgTCCATg-3' | 49 |
| | | 5'-AgCCATTCGCCggAATTC-3' | 50 |
| Human NF-kB | M62399&L19067 | 5'-gTgCACTACAgACgAgCC-3' | 51 |
| | | 5'-CTgCCATTCTgAAgCCgg-3' | 52 |
| | | 5'-ggCCCAgCTgCgACCCgg-3' | 53 |
| Human Rantes | | 5'-gAC CTT CAT ggT ACC TgT-3' | 54 |
| | | 5'-ACT CTC CAT CCT AgC TCA-3' | 55 |
| Human P38MAPK | NM001315 | 5'-TCT CCT gAg ACA TTT TCC-3' | 56 |
| | | 5'-ggT gCT CAg gAC TCC ATC-3' | 57 |
| Human Fas | NM000043 | 5'-gCC AAg UCA CUC gUA AAC-3' | 58 |
| | | 5'-gU CCA gAU gCC CAg CAU-3' | 59 |
| | | 5'-ACU CUA gAC CAA gCU UUg-3' | 60 |
| Human | NM000639 | 5'-ggg ACC CUg UUg CUg ACU-3' | 61 |
| Host genes | Aceession# | Antisense oligonucleotides | Seq H) |
| Fas-L | | 5'-CAU ggC AgC Ugg UgA gUC-3' | 62 |
| | | 5'-CCC AAA gUg CUU CUC UUA-3' | 63 |
| | | 5'-AAA gTg CTT CTC TTA gAg-3' | 64 |
| | | 5'-UUC UAC CgC CAg gCU CgA-3' | 65 |
| Human TACE | NM003183 | 5'-ACU gCC UCA UgU UCC Cgg-3' | 66 |
| | | 5'-CCU CAU gUU CCC ggC CCC-3' | 67 |
| | | 5'-ACU AAA UUA gCA CUC UgU-3' | 68 |
| | | 5'-CAg UUg Agg gUU gAg ACU-3' | 69 |
| Human TNF-R1 | NM001065 | 5'-gCC CAU gCC AgA CAg CUA-3' | 70 |
| | | 5'-gCg CAg CCU CAU CUg A-3' | 71 |
| | | 5'-ggg ggU CUg Uag UUg CUU-3' | 72 |
| | | 5'-CCA ggg gAg AgA ggg Ugg-3' | 73 |
| Human TNF-α | NM000594 | 5'-gCU CAU ggU gUC CUU UCC-3' | 74 |
| | | 5'-CAU gCU UUC AgU gCU CAU-3' | 75 |
| | | 5'-gAU gUU CgU CCU CCU CAC-3' | 76 |
| | | 5'-Agg AgC CgC gUC UgC ACU-3' | 77 |

TABLE 3 -continued

| Exemplary oligonucleotides targeted at animal host genes involved in response to influenza infection | | | |
|---|---|---|---|
| Human Caspase-3 | NM004346 | 5'-UUC UAC AAC CgC CUC ACA-3' | 78 |
| | | 5'-UCU CCA Ugg AUA CCU UUA-3' | 79 |
| | | 5'-ACC AAC CAU UUC UUUAgU-3' | 80 |
| | | 5'-CgU CUC gCU ACC gCC UgC-3' | 81 |
| Avian Fas | XM421659 | 5'-UCC CCg AgC CAU gUU CCC-3' | 82 |
| | | 5'-gCU AUg UCU CUU CCA AAC-3' | 83 |
| Avian Fas-L | AF296875 | 5'-CUg CAU ggC Ugg gAg Ugg-3' | 84 |
| | | 5'-CUC CAA CAg CAC CACUUA-3' | 85 |
| Avian TNF-α | AY 765397 | 5'-CAC UgC ACg CCC CAC AgC-3' | 86 |
| | | 5'-Agg AgC AgA CAU gAU AUA-3' | 87 |
| | | 5'-ACA CUg gCU AUA AAC gCU-3' | 88 |
| **Host genes** | **Accession#** | **Antisense oligonucleotides** | **Seq ID** |
| Avian TACE | NM001008682 | 5'-CAg CAC CUC ACg CCg CCC-3' | 89 |
| | | 5'-gAg UCU CAU ggU CCg AgC-3' | 90 |
| | | 5-ggA ggC AgC ggg ACA UCA-3' | 91 |
| Avian Caspase-3 | NM204725 | 5'-Ugg CUC UUg AUU AUC AgA-3' | 92 |
| | | 5'-UAU gUC UgU CAU CAU ggC-3' | 93 |
| | | 5'-UUA gCA Agg AAA gUA gAA-3' | 94 |

TABLE 4

Exemplary oligonucleotides targeted at the transcription start site of human host genes involved in response to influenza infection

| Target genes | Oligonucleotides | Seq ID |
|---|---|---|
| TACE | 5'-AAC gCC ACC TgC ACT TCT-3' | 95 |
| TNF-α | 5'-gCA gAC gCT CCC TCA g-3' | 96 |
| TNFR1 | 5'-TCT TCC TgT CCC gCT gTT-3' | 97 |
| IL6 | 5'-ggC TCA TTC TgC CCT CgA g-3' | 98 |
| NF-kB (p105/50) | 5'-AgC CAg gAA gTg AgA gAg-3' | 99 |
| NF-kB (p65) | 5'-CgC ATT TCC gCC TCT gg-3' | 100 |
| Rantes | 5'-CCC ACA ggT ACC ATg AAg-3' | 101 |
| P38MAPK | 5'-TTg CTg gCT CTT ggA ACC-3' | 102 |
| NF-IL6 | 5'-TTT AgC gAg TCA gAg CCg-3' | 103 |
| IL18 | 5'-CTT CCT CAT TCT CTC CCC-3' | 104 |
| IP-10 | 5'-AgC CCC ACg TTT TCT gAg-3' | 105 |
| CXCL-1 | 5'-TCg gAg AgC CAC AgA gCC-3' | 106 |
| IL-1b | 5'-gCA ATA CCA AAC CTC TTC-3' | 107 |
| Fas-L | 5'-AgA AAg AgA AAg ACA gAg-3' | 108 |
| Fas | 5'-CT CCCCCT CCC TACCCg Cg-3' | 109 |
| Caspase3 | 5'-gCT ggC gCT ggA ACA CAT-3' | 110 |

TABLE 5

| Exemplary combinations of target genes for antisense oligonucleotides Combinations |
|---|
| PA/NS1 |
| NS1/IP-10 |
| NS1/IL-1b |
| NS1/CXCL-1 |
| NS1/CXCL-1/Fas-L |
| PA/TNF-α |
| PA/TACE |
| PA/Caspase3 |
| NS1/Fas/IP-10 |
| NS1/Fas-L/PA |
| NS1/TNF-α/PA |
| NS1/TACE |
| NS1/Caspase3 |
| PA/NS1/Fas |
| PA/NS1/Fas-L |
| PA/NS1/TNF-α |
| PA/NS1/TACE |
| PA/NS1/Caspase3/CXCL-1 |
| PA/NS1/Fas/Fas-L |
| PA/NS1/Fas/Fas-L |
| PA/NS1/Fas/Fas-LTNF-α |
| PA/NS1/Fas/Fas-L/TNF-α/TACE |
| PA/NS1/Fas/Fas-L/TNF-α/TACE/Caspase3/CXCL-1/IP-10 |

TABLE 6

| Homeopathic RNA/DNA Dosages | |
|---|---|
| Dilution/Potency | μg/kg |
| 2x | 50 |
| 3% | 5 |
| 4x | 0.5 |
| 5x | 0.05 |
| 6x | 0.005 |

TABLE 7

Sequence of NS oligonucleotide and variants which bind with related strains of influenza.

| GENE IDENTIFICATION | SEQUENCE | SEQ ID NO |
|---|---|---|
| NS 526 | CCT CAg CAg TAT gTC CTg | 20 |
| Variant 1 | CCT CAC CAg TAT gTc CTg | 111 |
| Variant 2 | CCT CAT CAg TAT gTC CTg | 112 |

TABLE 8

Sequence of NS oligonucleotide and variants which bind with related strains of influenza.

| GENE IDENTIFICATION | SEQUENCE | SEQ ID NO |
|---|---|---|
| NS 705 | TCT TCA AAC TTC TgA CCT | 21 |
| Variant 3 | TCT TCA AAC TTT TgA CCT | 113 |
| Variant 4 | TCT TCG AAC TTC TgA CCT | 114 |

EXAMPLES

Example 1: Inhibition of II5N1 Influenza Virus in Chicken Embryo Fibroblast Cells The RNA oligonucleotides were tested in chicken embryo fibroblasts (CEF) for their effect on the replication of H5N1 influenza strain, and demonstrates a method of screening for active compounds.

Materials

Cells: CEF cells were prepared from 9-10 day's SPF chicken embryos.

RNA oligonucleotides: All the oligonucleotides were modified with 2'-O-methyl and 3'-butanol. The detailed sequences are shown in the following table (Table 9):

TABLE 9

RNA oligonucleotides used in the experiments.

| Oligo name | Target gene | Sequences | Seq ID No. |
|---|---|---|---|
| OE1 | NS1 | 5'-TTg TCA CCC TgC TTT TgC-3' | 14 |
| OE2 | NS1 | 5'-CAC AgT gTT Tgg ATC CAT-3' | 15 |
| OE3 | NS1 | 5'-CCT CAg CAg TAT gTC CTg-3' | 16 |
| OE4 | NS1 | 5'-TCT TCA AAC TTC TgA CCT-3' | 21 |
| OE5 | PA | 5'-CAT TTC gAA TCA gTA CCT gC-3' | 1 |
| OE6 | PA | 5'-TCC CTT CTC CTT COT gAC-3' | 2 |
| OE7 | PA | 5'-CAG CAC TgC CAT AAC TAT-3' | 3 |
| OE8 | NA | 5'-TCA TTT TgA ACT CCT gCT-3' | 30 |
| OE9 | M1 | 5'-TgA ggg ggC CTg ACg ggA-3' | 35 |
| OE10 | NP | 5'-AAg ACT CCC CgC CCC Tgg-3' | 25' |

Experimental Procedures

CEF cells were prepared from chicken embryos (9-10 days). After counting the cells, $1.5\times10^5$ cells in 0.5 ml were seeded into each well in a 24-well plate, cultured in 37 C° incubator with 5% $CO_2$ for 24 hr. The cells were then washed with PBS and transfected with RNA oligonucleotides (2 uM final concentration) in the presence of Lipofectamine 2000 (1% v/v) for 4 hr. The transfected cells were further washed with PBS and infected with H5N1 virus (5 $TCID_{50}$). CPE and HA assay were performed to determine the effect of the oligonucleotides.

Results

The viral titer was measured using HA assay and the inhibition rate was calculated as follows:

Inhibition (%)=100×(virus control testing group)/virus control.

As shown in Table 10, all the oligonucleotides exhibited anti-viral effect on the influenza virus replication.

TABLE 10

Screening of RNA oligonucleotides targeted at H5N1 strain in CEF

| RNA oligos | Viral Titer ($Log_2$eLD50) | Average titer ($Log_2$eLD50) | HA Units | Inhibition rate (%) |
|---|---|---|---|---|
| OE1 | 2, 0, 6 | 2.67 | 6.3 | 90 |
| OE2 | 0, 2, 0 | 0.67 | 1.6 | 97.5 |
| OE3 | 0, 4 | 2 | 4.0 | 94 |
| OE4 | 0, 0 | 0 | 1 | — |
| OE5 | 2, 0, 0 | 0.67 | 1.6 | 97.5 |
| OE6 | 2, 7 | 4.5 | 22 | 66 |
| OE7 | 6, 6, 4 | 5.3 | 39 | 39 |
| OE8 | 2, 6, 0 | 2.67 | 6.3 | 90 |
| OE9 | 2, 6 | 4 | 21 | 63 |
| OE10 | 2, 5, 2 | 4.5 | 22 | 67 |
| Oligo control | 6, 5 | 5.5 | 45 | 29.6 |
| Virus control | 6, 6 | 6.0 | 64 | 0 |
| CEF | 0, 0 | 0.0 | 0 | — |

Figure 2:
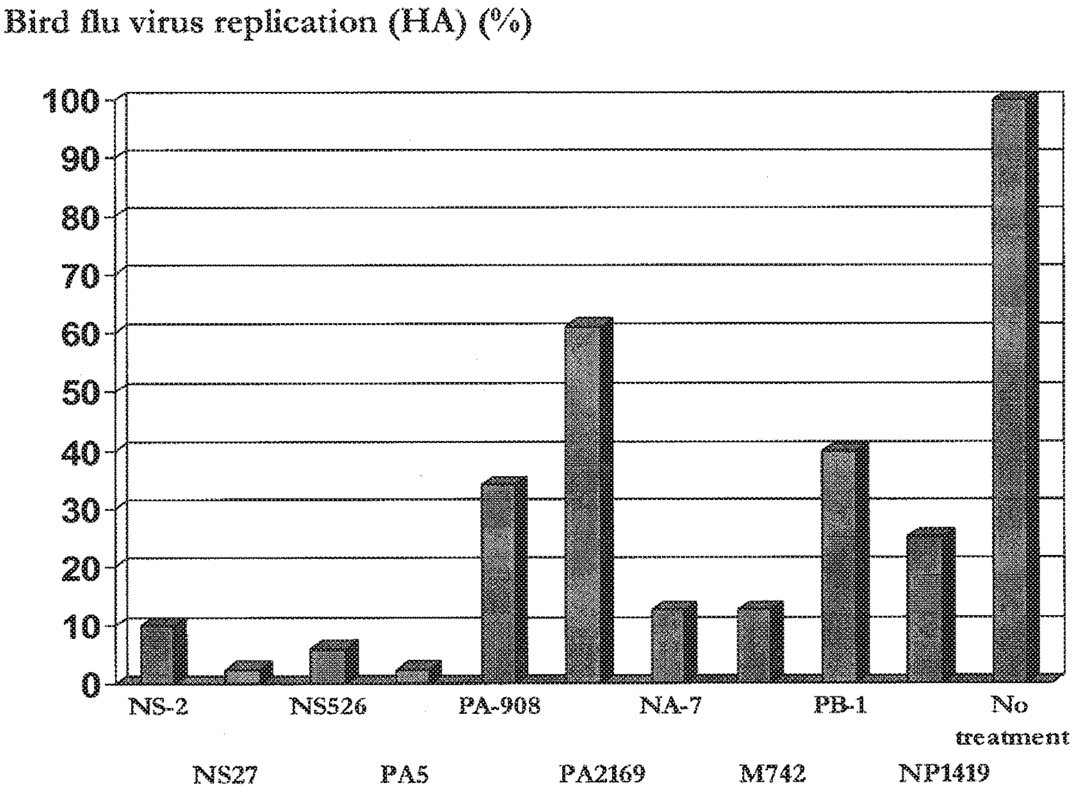
FIG. 2 is a graphical representation of inhibition of bird flu replication in CEF cells by treatment with microRNA targeting 10 different regions of viral genes compared with controls.

Example 2: Comparison of Inhibitory Effect of microRNA Oligonucleotides Upon Bird Flu Viral Infection in CEF Cells The experiment was run under the same conditions as in Example 1. In this experiment, single oligonucleotides targeting a wider variety of viral gene regions were utilized, including; NS-2, N27, NS526, PAS PA-908, PA2169, NA-7, M742, PB-1, and NP1419. HA assays were performed and the results given as percent inhibition, as shown in FIG. 2. The results demonstrate significant inhibition of viral replication by all of the oligonucleotides. Some of the oligonucleotides (i.e, those targeting NS-2, NS27, NS526, PA5, NA-7, M742) nearly eliminate viral replication.

Example 3: Comparison of the Antiviral Efficacy of Single and Combined Oligos in CEF Cells This experiment was performed based on the screening experiments. Five oligonucleotides (OE1, OE2, OE3, OE5 and OE6) were selected to compare the antiviral effect between single and combined oligonueleotide mixtures in CEF cells.

Materials

As in Example 1.

Experimental Procedure

The experiment was performed in with five oligo testing groups:

1) OE1
2) OE5
3) OE1+OE5
4) OE1+OE2+OE3+OE5
5) OE1+OE2+OE3+OE5+OE6

The final concentration of each combination was same at 2 uM.

Results

The following table (Table 11) summarized the results. The multiple oligonucleotide compositions demonstrated even stronger inhibition than compositions incorporating only one oligonucleotide sequence, further illustrating the benefit of targeting multiple genes or multiple sites in the same gene using RNA oligonucleotides.

TABLE 11

Comparison of single and combined oligos in CEF cells

| RNA Oligos | Virus titer Log$_2$eLD50) | | Average titer (Log$_2$eLD50) | HA Units | Inhibition (%) |
|---|---|---|---|---|---|
| OE1 | 2, 2, 2 | 1, 0, 0 | 1.17 | 2.25 | 55.17 |
| OE5 | 2, 0, 2 | 0, 2, 0 | 1 | 2.00 | 60.15 |
| OE1 + OE5 | 2, 0, 0 | 1, 0, 0 | 0.5 | 1.41 | 71.91 |
| OE1 + OE2 + OE3 + OE5 | 0, 0, 1 | 0, 1, 0 | 0.33 | 1.26 | 75.00 |
| OE1 + OE2 + OE3 + OE5 + OE6 | 0, 0, 0 | 0, 0, 1 | 0.17 | 1.13 | 77.50 |
| Oligo control | 1, 1, 3 | 2, 1, 2 | 1.67 | 3.18 | 36.65 |
| Virus control | 2, 3, 2 | 1, 2, 4 | 2.33 | 5.02 | 0.00 |
| CEF | 0, 0, 0 | 0, 0, 0 | 0 | 0.00 | — |

Example 4: Testing of RNA Oligos Against H5N1 Strain in Chickens

Compositions incorporating multiple RNA oligonucleotides targeting the NS gene were administered to animals (chickens) infected with the H5N1 strain.

Animals and Materials

1. SPF chickens at 12 days age
2. RNA Oligo Solution A (200 μg/100 μl in PBS)
3. RNA Oligo Solution B (RNA/Transfection reagent mixture)

(This solution is prepared on day 2)

Dilute OligoFectamine 1:1 in PBS;

Mixing the diluted OligoFectamine with 1 mM RNA oligos in 3:2, leave the mixture at RT for 20-30 min.

4. H5N1 Virus: titrated on chicken embryonic fibroblasts as defined as $eLD_{50}$ Experimental Procedure Day 1: Administered 100 μl of RNA oligo solution A by nasal drip to each chicken Day 2: Mixed 75 μl of RNA oligo solution B with 25 1.d of virus ($4\times10^3$ $eLD_{50}$) and administered to each chicken by nasal drip.

Day 3-8: Examined and recorded the well-being and death rate every six hours.

Day 8: Sacrificed the chickens and collected the lung tissues for plaque assay to determine the viral titers.

Results

Figure 3:
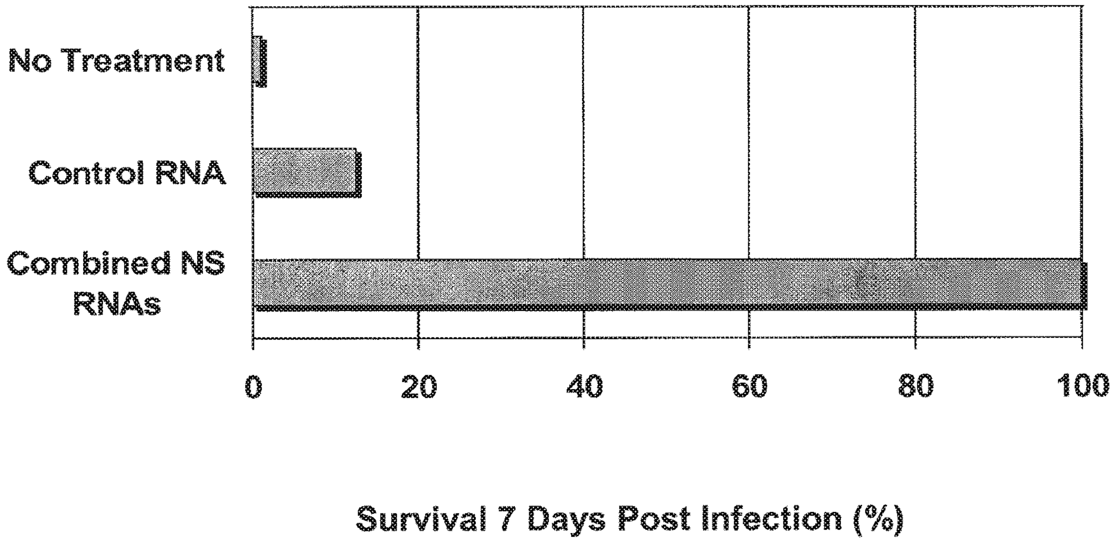
FIG. 3 is a graphical representation of survival in groups of chickens treated with a composition of multiple RNA oligonucleotides directed against NSI, mock treatment, or control and infected with H5N1 influenza virus.

Three NS1 oligos were mixed and tested in chickens (six animals per group). Compared with the controls, the treatment group showed 100% protection from the H5N1 infection as shown in FIG. 3.

Example 5: Antiviral Effect of RNA Oligonucleotides in Mice Infected with H5N1 Strain Animals and Materials 1. Mice with body weight between 18-20 grams were grouped (six mice for each group).
2. Compositions with multiple RNA oligonucleotides in solution were prepared by mixing different oligos at equal amount. Injection dose for each oligo was 100 ug/mouse.
3. H5N1 Virus: adapted in mice for three blind passages and LD50 was measured in mice. Challenge dose was 5 LD50.

Experimental Procedure

Day 1: Infected mice with 5 LD50 of H5N1 virus by nasal route.

Administered 50 μl of RNA oligonucleotides solution by nasal drip to each mouse

Day 3: Repeated RNA treatment

Day 3-12: Examined and recorded the body weight, body temperature, well-being and death rate every day.

Day 12: Sacrificed the mice and collected the lung tissues for plaque assay to determine the viral titers.

Results

Figure 4:
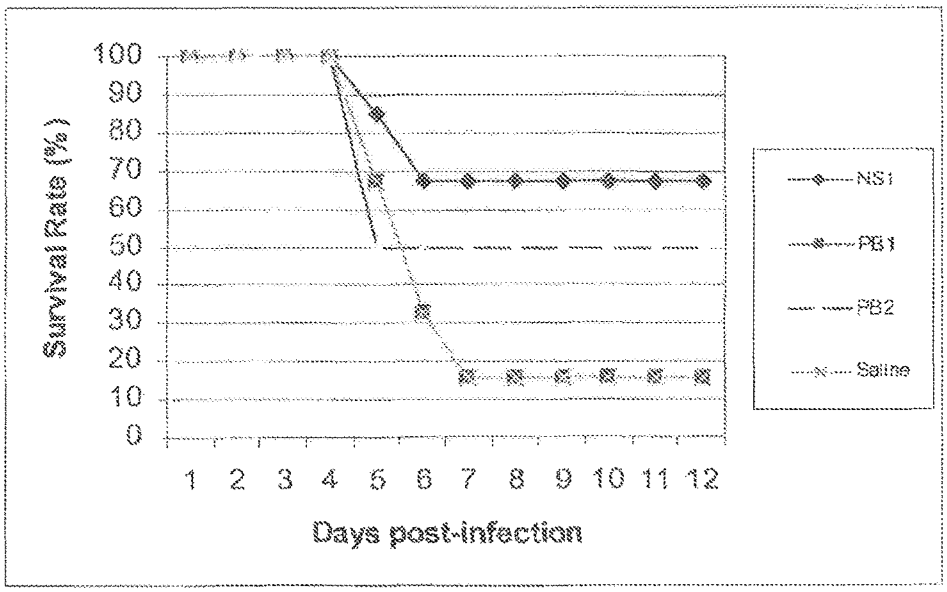
FIG. 4 is a graph depicting the survival of groups of mice treated with RNA oligonucleotides or saline after infection with H5N1 influenza virus.

Pools of RNA oligos targeted at PB1, PB2, and NS1 were tested in a murine model. The results shown in FIG. 4 demonstrate that both PB2 and NS1 RNA oligonucleotides protect mice from infection with the survival rate at 50% and 68% respectively.

Example 6: Toxicological Effect of RNA Oligonucleotides in Mice

Three groups of mice, 6-8 weeks old, were administered 100 mg/kg RNA compositions of the invention which pooled RNA oligos targeted at PB1, PB2 and NS1 genes. Each group of 5 were administered the above compositions daily, for a two weeks period via subcutaneous injection, intraperitoneal injection, and topical application, respectively. All groups maintained overall health demonstrating normal levels of activity and alertness during the experiment, with no abnormal behavior. No significant differences were observed in clinical chemistry results between test groups and control, for levels of alkaline phosphatase, AST, ALT, and indirect bilirubin. There was no evidence of toxicosis, nor renal or hepatic abnormalities. Upon sacrifice, there was no evidence of any organ enlargement, nor inflammation at site of injection. Histopathology revealed no differences between treated and control animals.

While preferred embodiments of the present invention have been shown and described herein, it will be obvious to those skilled in the art that such embodiments are provided by way of example. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A composition for treating an animal suffering from an influenza infection, the composition comprising:
 - at least one modified antisense oligonucleotide containing about 12 to about 26 contiguous ribose groups linked by achiral 5' to 3' internucleoside phosphodiester linkages, wherein
   - at least one ribose group of said at least one modified antisense oligonucleotide has a modified 2' substituent, wherein said 2' substituent is selected from the group consisting of methoxy, propoxy, methoxy-ethoxy, fluorine, chlorine, bromine, and iodine;
   - the 3' end of said at least one modified antisense oligonucleotide is end-blocked with an alkyl or an alcohol group;
   - said at least one modified antisense oligonucleotide is complementary to a region of an influenza virus gene that encodes a NS1 protein; and
   - wherein said antisense oligonucleotide is capable of inhibiting gene expression by blocking translation of mRNA; and
 - an excipient.

2. The composition of claim 1, wherein said composition comprises a plurality of modified oligonucleotides.

3. The composition of claim 2, wherein said plurality of oligonucleotides comprise:
 - more than one oligonucleotide targeted to a first influenza viral gene, wherein each of said more than one oligonucleotide targeted to a first influenza viral gene is independently complementary to the 5' UTR region, translational start site, the 3' UTR, or translational termination site of said first influenza viral gene; and
 - at least one oligonucleotide targeted to a second influenza viral gene, wherein each of said at least one oligonucleotide targeted to a second influenza viral gene is independently complementary to the 5' UTR region, translational start site, the 3' UTR, translational termination site or transcription start site of said second influenza viral gene.

4. The composition of claim 1, wherein at least one modified oligonucleotide comprises SEQ ID NO: 21.

5. The composition of claim 1, wherein said composition is suitable for oral administration.

6. The composition of claim 1, wherein said 2' substituent is selected from the group consisting of methoxy, propoxy, and methoxy-ethoxy.

7. The composition of claim 1, wherein said 3' end is end-blocked with a butanol.

8. The composition of claim 1, wherein said animal is human.

9. The composition of claim 1, wherein each ribose group of said at least one modified antisense oligonucleotide comprises a modified 2' substituent.

10. The composition of claim 9, wherein said 2' substituent of each said ribose group is methoxy, propoxy, or methoxy-ethoxy.

11. The composition of claim 1, wherein said composition is suitable for nasal administration.

12. The composition of claim 2, wherein each of said plurality of oligonucleotides is an antisense oligonucleotide.

13. The composition of claim 3, wherein each of said more than one oligonucleotide targeted to said first influenza viral gene is an antisense oligonucleotide.

14. The composition of claim 3, wherein each of said at least one oligonucleotide targeted to said second influenza viral gene is an antisense oligonucleotide.

15. The composition of claim 3, wherein said more than one oligonucleotide targeted to said first influenza viral gene comprises a combination of oligonucleotides complementary to the 5' UTR region, translational start site, the 3' UTR, and translational termination site of said first influenza viral gene.

16. The composition of claim 3, wherein said at least one oligonucleotide targeted to said second influenza viral gene comprises a combination of oligonucleotides complementary to the 5' UTR region, translational start site, the 3' UTR, translational termination site and transcription start site of said second influenza viral gene.

17. The composition of claim 1, wherein said composition is suitable for parenteral administration.

18. The composition of claim 1, wherein said at least one modified antisense oligonucleotide is a single modified antisense oligonucleotide, such that said composition comprises one modified antisense oligonucleotide.

19. The composition of claim 18, wherein said single modified antisense oligonucleotide contains about 12 to about 26 contiguous ribose groups linked by achiral 5' to 3' internucleoside phosphodiester linkages, and wherein each ribose group of said single modified antisense oligonucleotide comprises a 2'-O-methyl substitution;

the 3' end of said single modified antisense oligonucleotide comprises a butanol end-blocking group; and said single modified antisense oligonucleotide is complementary to a region of a H5N1 influenza virus gene that encodes a NS1 protein.

20. The composition of claim 19, wherein said single modified antisense oligonucleotide comprises nucleotides having the sequence of SEQ ID NO. 4, 5, 6, 7, 14, 20, 21, 111, 112, 113, or 114.

21. The composition of claim 20, wherein said single modified antisense oligonucleotide comprises nucleotides having the sequence of SEQ ID NO. 15, 16, 17, 18, 19, or 21.

* * * * *

SEQUENCE LISTING

<160> NUMBER OF SEQ ID NOS: 114

<210> SEQ ID NO 1
<211> LENGTH: 20
<212> TYPE: RNA
<213> ORGANISM: Influenza virus

<400> SEQUENCE: 1
cauuucgaau caguaccugc 20

<210> SEQ ID NO 2
<211> LENGTH: 18
<212> TYPE: RNA
<213> ORGANISM: Influenza virus

<400> SEQUENCE: 2
ucccuucucc uucgugac 18

<210> SEQ ID NO 3
<211> LENGTH: 18
<212> TYPE: RNA
<213> ORGANISM: Influenza virus

<400> SEQUENCE: 3
cagcacugcc auaacuau 18

<210> SEQ ID NO 4
<211> LENGTH: 18
<212> TYPE: DNA
<213> ORGANISM: Influenza virus

<400> SEQUENCE: 4
gggttgaagc attgtcgc 18

<210> SEQ ID NO 5
<211> LENGTH: 18
<212> TYPE: DNA
<213> ORGANISM: Influenza virus

<400> SEQUENCE: 5
cctccaggtg agtgcata 18

<210> SEQ ID NO 6
<211> LENGTH: 18
<212> TYPE: DNA
<213> ORGANISM: Influenza virus

<400> SEQUENCE: 6
cattcaaatg gtttgcct 18

<210> SEQ ID NO 7
<211> LENGTH: 18
<212> TYPE: DNA
<213> ORGANISM: Influenza virus

<400> SEQUENCE: 7
caattgctcg cctcttca 18

<210> SEQ ID NO 8
<211> LENGTH: 18
<212> TYPE: DNA
<213> ORGANISM: Influenza virus

<400> SEQUENCE: 8
ccctagacac catggcct 18

<210> SEQ ID NO 9
<211> LENGTH: 18
<212> TYPE: DNA
<213> ORGANISM: Influenza virus

<400> SEQUENCE: 9
ggacaagcta aattcact 18

<210> SEQ ID NO 10
<211> LENGTH: 18
<212> TYPE: DNA
<213> ORGANISM: Influenza virus

<400> SEQUENCE: 10
tctctccata ttgaatat 18

<210> SEQ ID NO 11
<211> LENGTH: 18
<212> TYPE: DNA
<213> ORGANISM: Influenza virus

<400> SEQUENCE: 11
tacagctagg ggagacac 18

<210> SEQ ID NO 12
<211> LENGTH: 18
<212> TYPE: DNA
<213> ORGANISM: Influenza virus

<400> SEQUENCE: 12
ttctggcagc gatgatca 18

<210> SEQ ID NO 13
<211> LENGTH: 18
<212> TYPE: DNA
<213> ORGANISM: Influenza virus

<400> SEQUENCE: 13
acactaattg atggccat 18

<210> SEQ ID NO 14
<211> LENGTH: 18
<212> TYPE: RNA
<213> ORGANISM: Influenza virus

<400> SEQUENCE: 14
uugucacccu gcuuuugc 18

<210> SEQ ID NO 15
<211> LENGTH: 18
<212> TYPE: RNA
<213> ORGANISM: Influenza virus

<400> SEQUENCE: 15
cacaguguuu ggauccau 18

<210> SEQ ID NO 16
<211> LENGTH: 18
<212> TYPE: RNA
<213> ORGANISM: Influenza virus -continued

<400> SEQUENCE: 16
ccucagcagu auguccug 18

<210> SEQ ID NO 17
<211> LENGTH: 18
<212> TYPE: RNA
<213> ORGANISM: Influenza virus

<400> SEQUENCE: 17
ucuucaaacu ucugaccu 18

<210> SEQ ID NO 18
<211> LENGTH: 16
<212> TYPE: DNA
<213> ORGANISM: Influenza virus

<400> SEQUENCE: 18
ttgtcaccct gctttt 16

<210> SEQ ID NO 19
<211> LENGTH: 14
<212> TYPE: DNA
<213> ORGANISM: Influenza virus

<400> SEQUENCE: 19
ttgtcaccct gctt 14

<210> SEQ ID NO 20
<211> LENGTH: 18
<212> TYPE: DNA
<213> ORGANISM: Influenza virus

<400> SEQUENCE: 20
cctcatcagt atgtcctg 18

<210> SEQ ID NO 21
<211> LENGTH: 18
<212> TYPE: DNA
<213> ORGANISM: Influenza virus

<400> SEQUENCE: 21
tcttcaaact tctgacct 18

<210> SEQ ID NO 22
<211> LENGTH: 18
<212> TYPE: DNA
<213> ORGANISM: Influenza virus

<400> SEQUENCE: 22
gacgccatga tgttgatg 18

<210> SEQ ID NO 23
<211> LENGTH: 18
<212> TYPE: DNA
<213> ORGANISM: Influenza virus

<400> SEQUENCE: 23
cccctttact gctgcacc 18

<210> SEQ ID NO 24
<211> LENGTH: 18
<212> TYPE: DNA
<213> ORGANISM: Influenza virus

<400> SEQUENCE: 24
tgctctttgt gctgctgt 18

<210> SEQ ID NO 25
<211> LENGTH: 18
<212> TYPE: DNA
<213> ORGANISM: Influenza virus

<400> SEQUENCE: 25
aagactcccc gcccctgg 18

<210> SEQ ID NO 26
<211> LENGTH: 21
<212> TYPE: DNA
<213> ORGANISM: Influenza virus

<400> SEQUENCE: 26
ctccattttg acagattgaa c 21

<210> SEQ ID NO 27
<211> LENGTH: 18
<212> TYPE: DNA
<213> ORGANISM: Influenza virus

<400> SEQUENCE: 27
gtcaacctgc tctgtcga 18

<210> SEQ ID NO 28
<211> LENGTH: 18
<212> TYPE: DNA
<213> ORGANISM: Influenza virus

<400> SEQUENCE: 28
aaatcccctg ggtaacag 18

<210> SEQ ID NO 29
<211> LENGTH: 18
<212> TYPE: DNA
<213> ORGANISM: Influenza virus

<400> SEQUENCE: 29
tgaatccccc acagtacc 18

<210> SEQ ID NO 30
<211> LENGTH: 18
<212> TYPE: DNA
<213> ORGANISM: Influenza virus

<400> SEQUENCE: 30
tcattttgaa ctcctgct 18

<210> SEQ ID NO 31
<211> LENGTH: 18
<212> TYPE: DNA
<213> ORGANISM: Influenza virus

<400> SEQUENCE: 31
acagattgat ccgatggt 18

<210> SEQ ID NO 32
<211> LENGTH: 18
<212> TYPE: DNA
<213> ORGANISM: Influenza virus

<400> SEQUENCE: 32 ccccttgga accgatcc 18

<210> SEQ ID NO 33
<211> LENGTH: 18
<212> TYPE: DNA
<213> ORGANISM: Influenza virus

<400> SEQUENCE: 33
gtacttcact acagccac 18

<210> SEQ ID NO 34
<211> LENGTH: 18
<212> TYPE: DNA
<213> ORGANISM: Influenza virus

<400> SEQUENCE: 34
cggttagaag actcatct 18

<210> SEQ ID NO 35
<211> LENGTH: 18
<212> TYPE: DNA
<213> ORGANISM: Influenza virus

<400> SEQUENCE: 35
tgagggggcc tgacggga 18

<210> SEQ ID NO 36
<211> LENGTH: 18
<212> TYPE: DNA
<213> ORGANISM: Influenza virus

<400> SEQUENCE: 36
cgtctacgct gcagtcct 18

<210> SEQ ID NO 37
<211> LENGTH: 18
<212> TYPE: DNA
<213> ORGANISM: Influenza virus

<400> SEQUENCE: 37
gtaggcctgc aaattttc 18

<210> SEQ ID NO 38
<211> LENGTH: 18
<212> TYPE: DNA
<213> ORGANISM: Influenza virus

<400> SEQUENCE: 38
gcagcgcggg ccatgggg 18

<210> SEQ ID NO 39
<211> LENGTH: 18
<212> TYPE: DNA
<213> ORGANISM: Influenza virus

<400> SEQUENCE: 39
ggtcagttgg atttgtca 18

<210> SEQ ID NO 40
<211> LENGTH: 18
<212> TYPE: DNA
<213> ORGANISM: Influenza virus

<400> SEQUENCE: 40
gccatggctg cttcagac 18

<210> SEQ ID NO 41
<211> LENGTH: 18
<212> TYPE: DNA
<213> ORGANISM: Influenza virus

<400> SEQUENCE: 41
ggtacagctc tctttagg 18

<210> SEQ ID NO 42
<211> LENGTH: 18
<212> TYPE: DNA
<213> ORGANISM: Influenza virus

<400> SEQUENCE: 42
ttgattcatg gtgctgag 18

<210> SEQ ID NO 43
<211> LENGTH: 18
<212> TYPE: DNA
<213> ORGANISM: Influenza virus

<400> SEQUENCE: 43
tcccctctgg ttttaagg 18

<210> SEQ ID NO 44
<211> LENGTH: 18
<212> TYPE: DNA
<213> ORGANISM: Influenza virus

<400> SEQUENCE: 44
cagcagccat ctttattc 18

<210> SEQ ID NO 45
<211> LENGTH: 18
<212> TYPE: DNA
<213> ORGANISM: Influenza virus

<400> SEQUENCE: 45
agctagtctt cgttttga 18

<210> SEQ ID NO 46
<211> LENGTH: 18
<212> TYPE: DNA
<213> ORGANISM: Influenza virus

<400> SEQUENCE: 46
ctctttcgtr cccggtgg 18

<210> SEQ ID NO 47
<211> LENGTH: 18
<212> TYPE: DNA
<213> ORGANISM: Influenza virus

<400> SEQUENCE: 47
aaggagttca tagctggg 18

<210> SEQ ID NO 48
<211> LENGTH: 18
<212> TYPE: DNA
<213> ORGANISM: Influenza virus

<400> SEQUENCE: 48
ccatgctaca tttgccga 18

<210> SEQ ID NO 49
<211> LENGTH: 16
<212> TYPE: DNA
<213> ORGANISM: Influenza virus

<400> SEQUENCE: 49
gaacagttcg tccatg 16

<210> SEQ ID NO 50
<211> LENGTH: 18
<212> TYPE: DNA
<213> ORGANISM: Influenza virus

<400> SEQUENCE: 50
agccattcgc cggaattc 18

<210> SEQ ID NO 51
<211> LENGTH: 18
<212> TYPE: DNA
<213> ORGANISM: Influenza virus

<400> SEQUENCE: 51
gtgcactaca gacgagcc 18

<210> SEQ ID NO 52
<211> LENGTH: 18
<212> TYPE: DNA
<213> ORGANISM: Influenza virus

<400> SEQUENCE: 52
ctgccattct gaagccgg 18

<210> SEQ ID NO 53
<211> LENGTH: 18
<212> TYPE: DNA
<213> ORGANISM: Influenza virus

<400> SEQUENCE: 53
ggcccagctg cgacccgg 18

<210> SEQ ID NO 54
<211> LENGTH: 18
<212> TYPE: DNA
<213> ORGANISM: Influenza virus

<400> SEQUENCE: 54
gaccttcatg gtacctgt 18

<210> SEQ ID NO 55
<211> LENGTH: 18
<212> TYPE: DNA
<213> ORGANISM: Influenza virus

<400> SEQUENCE: 55
actctccatc ctagctca 18

<210> SEQ ID NO 56
<211> LENGTH: 18
<212> TYPE: DNA
<213> ORGANISM: Influenza virus

<400> SEQUENCE: 56
tctcctgaga cattttcc 18

<210> SEQ ID NO 57
<211> LENGTH: 18
<212> TYPE: DNA
<213> ORGANISM: Influenza virus

<400> SEQUENCE: 57
ggtgctcagg actccatc 18

<210> SEQ ID NO 58
<211> LENGTH: 18
<212> TYPE: RNA
<213> ORGANISM: Influenza virus

<400> SEQUENCE: 58
gccaagucac ucguaaac 18

<210> SEQ ID NO 59
<211> LENGTH: 17
<212> TYPE: RNA
<213> ORGANISM: Influenza virus

<400> SEQUENCE: 59
guccagaugc ccagcau 17

<210> SEQ ID NO 60
<211> LENGTH: 18
<212> TYPE: RNA
<213> ORGANISM: Influenza virus

<400> SEQUENCE: 60
acucuagacc aagcuuug 18

<210> SEQ ID NO 61
<211> LENGTH: 18
<212> TYPE: RNA
<213> ORGANISM: Influenza virus

<400> SEQUENCE: 61
gggacccugu ugcugacu 18

<210> SEQ ID NO 62
<211> LENGTH: 18
<212> TYPE: RNA
<213> ORGANISM: Influenza virus

<400> SEQUENCE: 62
cauggcagcu ggugaguc 18

<210> SEQ ID NO 63
<211> LENGTH: 18
<212> TYPE: RNA
<213> ORGANISM: Influenza virus

<400> SEQUENCE: 63
cccaaagugc uucucuua 18

<210> SEQ ID NO 64
<211> LENGTH: 18
<212> TYPE: DNA
<213> ORGANISM: Influenza virus

<400> SEQUENCE: 64
aaagtgcttc tcttagag 18

<210> SEQ ID NO 65
<211> LENGTH: 18
<212> TYPE: RNA
<213> ORGANISM: Influenza virus

<400> SEQUENCE: 65
uucuaccgcc aggcucga 18

<210> SEQ ID NO 66
<211> LENGTH: 18
<212> TYPE: RNA
<213> ORGANISM: Influenza virus

<400> SEQUENCE: 66
acugccucau guucccgg 18

<210> SEQ ID NO 67
<211> LENGTH: 18
<212> TYPE: RNA
<213> ORGANISM: Influenza virus

<400> SEQUENCE: 67
ccucauguuc ccggcccc 18

<210> SEQ ID NO 68
<211> LENGTH: 18
<212> TYPE: RNA
<213> ORGANISM: Influenza virus

<400> SEQUENCE: 68
acuaaauuag cacucugu 18

<210> SEQ ID NO 69
<211> LENGTH: 18
<212> TYPE: RNA
<213> ORGANISM: Influenza virus

<400> SEQUENCE: 69
caguugaggg uugagacu 18

<210> SEQ ID NO 70
<211> LENGTH: 18
<212> TYPE: RNA
<213> ORGANISM: Influenza virus

<400> SEQUENCE: 70
gcccaugcca gacagcua 18

<210> SEQ ID NO 71
<211> LENGTH: 16
<212> TYPE: RNA
<213> ORGANISM: Influenza virus

<400> SEQUENCE: 71
gcgcagccuc aucuga 16

<210> SEQ ID NO 72
<211> LENGTH: 18
<212> TYPE: RNA
<213> ORGANISM: Influenza virus

<400> SEQUENCE: 72
gggggucugu aguugcuu 18

<210> SEQ ID NO 73
<211> LENGTH: 18
<212> TYPE: RNA
<213> ORGANISM: Influenza virus

<400> SEQUENCE: 73
ccaggggaga gagggugg 18

<210> SEQ ID NO 74
<211> LENGTH: 18
<212> TYPE: RNA
<213> ORGANISM: Influenza virus

<400> SEQUENCE: 74
gcucauggug uccuuucc 18

<210> SEQ ID NO 75
<211> LENGTH: 18
<212> TYPE: RNA
<213> ORGANISM: Influenza virus

<400> SEQUENCE: 75
caugcuuuca gugcucau 18

<210> SEQ ID NO 76
<211> LENGTH: 18
<212> TYPE: RNA
<213> ORGANISM: Influenza virus

<400> SEQUENCE: 76
gauguucguc cuccucac 18

<210> SEQ ID NO 77
<211> LENGTH: 18
<212> TYPE: RNA
<213> ORGANISM: Influenza virus

<400> SEQUENCE: 77
aggagccgcg ucugcacu 18

<210> SEQ ID NO 78
<211> LENGTH: 18
<212> TYPE: RNA
<213> ORGANISM: Influenza virus

<400> SEQUENCE: 78
uucuacaacc gccucaca 18

<210> SEQ ID NO 79
<211> LENGTH: 18
<212> TYPE: RNA
<213> ORGANISM: Influenza virus

<400> SEQUENCE: 79
ucuccaugga uaccuuua 18

<210> SEQ ID NO 80
<211> LENGTH: 18
<212> TYPE: RNA
<213> ORGANISM: Influenza virus

<400> SEQUENCE: 80
accaaccauu ucuuuagu 18

<210> SEQ ID NO 81
<211> LENGTH: 18
<212> TYPE: RNA
<213> ORGANISM: Avian influenza virus

<400> SEQUENCE: 81
cgucucgcua ccgccugc 18

<210> SEQ ID NO 82
<211> LENGTH: 18
<212> TYPE: RNA
<213> ORGANISM: Avian influenza virus

<400> SEQUENCE: 82
uccccgagcc auguuccc 18

<210> SEQ ID NO 83
<211> LENGTH: 18
<212> TYPE: RNA
<213> ORGANISM: Avian influenza virus

<400> SEQUENCE: 83
gcuaugucuc uuccaaac 18

<210> SEQ ID NO 84
<211> LENGTH: 18
<212> TYPE: RNA
<213> ORGANISM: Avian influenza virus

<400> SEQUENCE: 84
cugcauggcu gggagugg 18

<210> SEQ ID NO 85
<211> LENGTH: 18
<212> TYPE: RNA
<213> ORGANISM: Avian influenza virus

<400> SEQUENCE: 85
cuccaacagc accacuua 18

<210> SEQ ID NO 86
<211> LENGTH: 18
<212> TYPE: RNA
<213> ORGANISM: Avian influenza virus

<400> SEQUENCE: 86
cacugcacgc cccacagc 18

<210> SEQ ID NO 87
<211> LENGTH: 18
<212> TYPE: RNA
<213> ORGANISM: Avian influenza virus

<400> SEQUENCE: 87
aggagcagac augauaua 18

<210> SEQ ID NO 88
<211> LENGTH: 18
<212> TYPE: RNA
<213> ORGANISM: Avian influenza virus

<400> SEQUENCE: 88
acacuggcua uaaacgcu 18

<210> SEQ ID NO 89
<211> LENGTH: 18
<212> TYPE: RNA
<213> ORGANISM: Avian influenza virus

<400> SEQUENCE: 89
cagcaccuca cgccgccc 18

<210> SEQ ID NO 90
<211> LENGTH: 18
<212> TYPE: RNA
<213> ORGANISM: Avian influenza virus

<400> SEQUENCE: 90
gagucucaug guccgagc 18

<210> SEQ ID NO 91
<211> LENGTH: 18
<212> TYPE: RNA
<213> ORGANISM: Avian influenza virus

<400> SEQUENCE: 91
ggaggcagcg ggacauca 18

<210> SEQ ID NO 92
<211> LENGTH: 18
<212> TYPE: RNA
<213> ORGANISM: Avian influenza virus

<400> SEQUENCE: 92
uggcucuuga uuaucaga 18

<210> SEQ ID NO 93
<211> LENGTH: 18
<212> TYPE: RNA
<213> ORGANISM: Avian influenza virus

<400> SEQUENCE: 93
uaugucuguc aucauggc 18

<210> SEQ ID NO 94
<211> LENGTH: 18
<212> TYPE: RNA
<213> ORGANISM: Avian influenza virus

<400> SEQUENCE: 94
uuagcaagga aaguagaa 18

<210> SEQ ID NO 95
<211> LENGTH: 18
<212> TYPE: DNA
<213> ORGANISM: Influenza virus

<400> SEQUENCE: 95
aacgccacct gcacttct 18

<210> SEQ ID NO 96
<211> LENGTH: 16
<212> TYPE: DNA
<213> ORGANISM: Influenza virus

<400> SEQUENCE: 96
gcagacgctc cctcag 16

<210> SEQ ID NO 97
<211> LENGTH: 18
<212> TYPE: DNA
<213> ORGANISM: Influenza virus

<400> SEQUENCE: 97
tcttcctgtc ccgctgtt 18

<210> SEQ ID NO 98
<211> LENGTH: 19
<212> TYPE: DNA
<213> ORGANISM: Influenza virus

<400> SEQUENCE: 98
ggctcattct gccctcgag 19

<210> SEQ ID NO 99
<211> LENGTH: 18
<212> TYPE: DNA
<213> ORGANISM: Influenza virus

<400> SEQUENCE: 99
agccaggaag tgagagag 18

<210> SEQ ID NO 100
<211> LENGTH: 17
<212> TYPE: DNA
<213> ORGANISM: Influenza virus

<400> SEQUENCE: 100
cgcatttccg cctctgg 17

<210> SEQ ID NO 101
<211> LENGTH: 18
<212> TYPE: DNA
<213> ORGANISM: Influenza virus

<400> SEQUENCE: 101
cccacaggta ccatgaag 18

<210> SEQ ID NO 102
<211> LENGTH: 18
<212> TYPE: DNA
<213> ORGANISM: Influenza virus

<400> SEQUENCE: 102
ttgctggctc ttggaacc 18

<210> SEQ ID NO 103
<211> LENGTH: 18
<212> TYPE: DNA
<213> ORGANISM: Influenza virus

<400> SEQUENCE: 103
tttagcgagt cagagccg 18

<210> SEQ ID NO 104
<211> LENGTH: 18
<212> TYPE: DNA
<213> ORGANISM: Influenza virus

<400> SEQUENCE: 104
cttcctcatt ctctcccc 18

<210> SEQ ID NO 105
<211> LENGTH: 18
<212> TYPE: DNA
<213> ORGANISM: Influenza virus

<400> SEQUENCE: 105
agccccacgt tttctgag 18

<210> SEQ ID NO 106
<211> LENGTH: 18
<212> TYPE: DNA
<213> ORGANISM: Influenza virus

<400> SEQUENCE: 106
tcggagagcc acagagcc 18

<210> SEQ ID NO 107
<211> LENGTH: 18
<212> TYPE: DNA
<213> ORGANISM: Influenza virus

<400> SEQUENCE: 107
gcaataccaa acctcttc 18

<210> SEQ ID NO 108
<211> LENGTH: 18
<212> TYPE: DNA
<213> ORGANISM: Influenza virus

<400> SEQUENCE: 108
agaaagagaa agacagag 18

<210> SEQ ID NO 109
<211> LENGTH: 19
<212> TYPE: DNA
<213> ORGANISM: Influenza virus

<400> SEQUENCE: 109
ctccccctcc ctacccgcg 19

<210> SEQ ID NO 110
<211> LENGTH: 18
<212> TYPE: DNA
<213> ORGANISM: Influenza virus

<400> SEQUENCE: 110
gctggcgctg gaacacat 18

<210> SEQ ID NO 111
<211> LENGTH: 18
<212> TYPE: DNA
<213> ORGANISM: Influenza virus

<400> SEQUENCE: 111
cctcaccagt atgtcctg 18

<210> SEQ ID NO 112
<211> LENGTH: 18
<212> TYPE: DNA
<213> ORGANISM: Influenza virus -continued

```
<400> SEQUENCE: 112

cctcatcagt atgtcctg                                              18


<210> SEQ ID NO 113
<211> LENGTH: 18
<212> TYPE: DNA
<213> ORGANISM: Influenza virus

<400> SEQUENCE: 113

tcttcaaact tttgacct                                              18


<210> SEQ ID NO 114
<211> LENGTH: 18
<212> TYPE: DNA
<213> ORGANISM: Influenza virus

<400> SEQUENCE: 114

tcttcgaact tctgacct                                              18
```